United States Patent [19]
Chamberlain et al.

[11] Patent Number: 6,004,817
[45] Date of Patent: Dec. 21, 1999

[54] METHOD FOR MEASURING STRESS LEVELS IN POLYMERIC COMPOSITIONS

[75] Inventors: Craig S. Chamberlain, Woodbury; Dean E. Feyma, Sandstone; Steven J. Heilig; Elaine M. Yorkgitis, both of St. Paul, all of Minn.

[73] Assignee: 3M Innovative Properties Company, St. Paul, Minn.

[21] Appl. No.: 08/832,652

[22] Filed: Apr. 4, 1997

[51] Int. Cl.$^6$ .................................................. G01N 27/72
[52] U.S. Cl. .................... 436/56; 73/779; 324/207.21; 324/207.22; 324/209; 324/219; 436/149
[58] Field of Search .................. 436/56, 149; 73/582, 73/149, 779, 768, 827, DIG. 2; 324/219, 226, 71.1, 200, 207.21, 207.22, 209

[56] References Cited

U.S. PATENT DOCUMENTS

| | | |
|---|---|---|
| 4,131,064 | 12/1978 | Ryan et al. |
| 4,618,525 | 10/1986 | Chamberlain et al. |
| 4,944,185 | 7/1990 | Clark, Jr et al. |
| 5,409,968 | 4/1995 | Clatanoff et al. |
| 5,453,291 | 9/1995 | Sasahara et al. |
| 5,504,281 | 4/1996 | Whitney et al. |
| 5,640,088 | 6/1997 | Sasahara et al. |

FOREIGN PATENT DOCUMENTS 2 219 405  12/1989  United Kingdom .

OTHER PUBLICATIONS

Abstract of SU-A-1597614, XP-002070371 of Derwent Database.

Giurgiutiu et al., J. Intell. Mater. Syst. Struct. (1996) 7(6), 623-634, Nov. 1996.

Zhou et al., Proc. 36th AIAA/ASME/AHS/ASC Structures Structural Dynamics and Materials Conference, New Orleans, Apr. 9-12, 1995, Paper No. AIAA-95-1105-CP.

Lekatou et al., J. Mater. Res., vol. 11, No. 5 pp. 1293-1304, May 1996.

Walther, IEEE 1989 Natl. Symp. on Electromagnetic Compatibility, Denver Co., May 23-25 1989, Session 2C pp. 41-45.

S. Zhou et al., "An in-situ sensory technique for in-service quality monitoring—measurement of the complex Young's modulus of polymers," SPIE vol. 1918, (1993), pp. 14-23.

F.P. Sun et al., "Magnetic activation of embedded sensory particles in active tagging interrogation of adhesive bonding," SPIE vol. 1918, (1993), pp. 400-409.

W.G. Clark, Jr., "Magnetic Particle Tagging for Process Control in Composite Fabrication,"Non-destructive Evaluation Applied to Process Control of Composite Fabrication, 1995.

W.G. Clark, Jr., "Magnetic Tagging Monitors Bond Integrity and Thickness," Adhesives Age, Jun. 1992, pp. 22-27.

T.W. Barbee et al., "Microstructure of Amorphous 304 Stainless Steel-Carbon Alloys Synthesized By Magnetron Sputter Deposition", *Thin Solid Films* 63 (1979), pp. 143-150.

(List continued on next page.)

*Primary Examiner*—Jan Ludlow
*Attorney, Agent, or Firm*—Brian E. Szymanski

[57] ABSTRACT

A method for measuring the level of stress in a polymeric or pre-polymeric composition within a given volume that includes combining the polymeric or pre-polymeric composition with a plurality of microparticles having a non-ferromagnetic or non-ferrimagnetic core provided with a coating that is ferromagnetic or ferrimagnetic to form an admixture in which the microparticles are substantially uniformly dispersed throughout the composition. The microparticles have a detectable magnetic characteristic which correlates with level of stress in the composition within a given volume. The change in the magnetic characteristic of the microparticles is then measured to determine the level of stress in the composition within a given volume.

34 Claims, 11 Drawing Sheets

OTHER PUBLICATIONS

V. Giurgiutiu et al., "Passive and active tagging of reinforced composites for in process and in-field non-destructive evaluation," SPIE vol. 2717, (1996), pp. 361–371.

S. Zhou et al., "Review of Embedded Particle Tagging Methods for NDE of Composite Materials and Structures," SPIE vol. 2444, (1995), pp. 39–52.

W. G. Clark, Jr. et al., "Tagging Lets You Test the Untestable," *Advanced Materials & Processes*, Apr. 1990, pp. 59–69.

METHOD FOR MEASURING STRESS LEVELS IN POLYMERIC COMPOSITIONS

BACKGROUND OF THE INVENTION

The invention relates to measuring stress levels in polymers or polymeric compositions.

Processes for manufacturing polymeric compositions (e.g., adhesives such as structural adhesives) often require adding or combining precise amounts of pre-polymeric components forming these compositions, particularly where these components react together to form the composition. Devices dispensing these components can malfunction periodically and/or systematically, resulting in the deposition of an incorrect mix of the components. These malfunctions can significantly affect the quality of the resulting products.

It is also desirable to be able to measure the quantity of polymeric or pre-polymeric material in any given volume of an article incorporating the material. For example, in the case of a structural adhesive joining two substrates together, it is desirable to measure the thickness of the adhesive throughout the adhesive joint to determine whether the thickness is uniform. Non-uniformities can affect the performance of the joint, causing it to under perform in some circumstances.

It is also desirable to be able to measure the level of stress in a polymer or polymeric composition or substrate.

SUMMARY OF THE INVENTION

In general, the invention features a method for measuring the level of stress in polymers or polymeric compositions within a given volume that includes providing a polymeric or pre-polymeric composition containing a plurality of microparticles having a non-ferromagnetic or non-ferrimagnetic core provided with a coating that is ferromagnetic or ferrimagnetic wherein the microparticles are substantially uniformly dispersed throughout the composition. The microparticles have a detectable magnetic characteristic which correlates with the level of stress in the composition.

In another aspect, the invention provides a method for measuring the level of stress in polymers or polymeric compositions within a given volume that includes combining the polymeric or pre-polymeric composition with a plurality of microparticles having a non-ferromagnetic or non-ferrimagnetic core provided with a coating that is ferromagnetic or ferrimagnetic to form an admixture in which the microparticles are substantially uniformly dispersed throughout the composition. The microparticles have a detectable magnetic characteristic which correlates with the level of stress in the composition.

In another aspect, the invention provides a method for determining the stress level in said admixture during dispensing of said admixture.

In another aspect, the invention provides a method for determining the stress level in a polymeric reaction mixture.

In another aspect, the invention provides a method of measuring inductance or inductive reactance of a sample comprising the steps of measuring the inductance or the inductive reactance of the sample; and correcting said measurement of inductance or inductive reactance for temperature.

As used herein, a "pre-polymeric composition" refers both to compositions whose molecular weight has not been sufficiently advanced to qualify as a polymeric composition (e.g., partially polymerized pre-polymeric syrups), as well as individual reactants in the form of monomers or oligomers that react with themselves or with other reactants to form a polymeric composition.

In preferred embodiments, the core of the microparticles is selected from the group consisting of glass bubbles, glass beads, glass fibers, fumed silica particles, fused silica particles, mica flakes, polymeric particles, and combinations thereof, with glass bubbles being particularly preferred. The coating (which may be provided over substantially all or a portion of the surface of the core) is preferably a ferromagnetic or ferrimagnetic material. Examples of suitable ferromagnetic or ferrimagnetic materials include nickel, iron, alloys thereof, and oxides thereof. Stainless steel coatings are particularly preferred.

The microparticles preferably have an average major dimension between about 10 micrometers and about 1 millimeter. The average thickness of the coating preferably ranges from about 0.1 nanometers to about 5 micrometers, more preferably from about 1 nanometer to about 200 nanometers. The amount of microparticles provided in the admixture preferably ranges between about 0.01 and 50% by volume.

In one preferred embodiment, the method of the invention is used to determine the level of externally applied forces on the composition.

In another preferred embodiment, the method of the invention is used to measure the degree of cure of an adhesive composition.

In another embodiment, the method of the invention is used to determine the quality of adhesion of an adhesive or adhesive composition to a substrate.

In another embodiment, the method of invention is used to determine the direction of internal stress of a polymeric composition.

One example of a useful polymeric composition is an adhesive composition. Specific examples of preferred polymeric compositions include epoxy resins (e.g., base-cured epoxies, acid-cured epoxies, and addition-cured epoxies), polyurethanes, acrylates, polyorganosiloxanes, and phenolics.

The invention provides a reliable method for measuring the levels of stress in a polymeric or pre-polymeric composition within a given volume using microparticle "tags" having a detectable magnetic characteristic. The measurement of the stress level in a polymeric composition can then be correlated with and used to determine, for example, the degree of cure of an adhesive or polymer composition, the level of applied external forces, the level or quality of adhesion of an adhesive to a substrate and the internal stress due to heating and cooling cycles. The microparticles are easily fabricated and are generally chemically inert and stable over reasonable periods of time. The microparticles can also be used to determine the volume of the composition as described in copending patent application entitled "Method for Measuring the Quantity of a Polymeric or Pre-polymeric Composition," U.S. application Ser. No. 08/610,605, filed on Mar. 8, 1996, the entire contents of which is incorporated herein by reference.

Moreover, certain properties of the microparticles are very similar to those of their uncoated counterparts. For example, metal-coated glass microbubbles impart substantially the same rheological behavior and mechanical properties as their uncoated counterparts. Thus, the microparticles can be substituted virtually one-for-one for their uncoated counterparts on a volume basis without adversely affecting the properties of the final composition.

Other features and advantages of the invention will be apparent from the following description of the preferred embodiments thereof, and from the claims.

DESCRIPTION OF THE PREFERRED EMBODIMENTS

Materials

Figure 1:
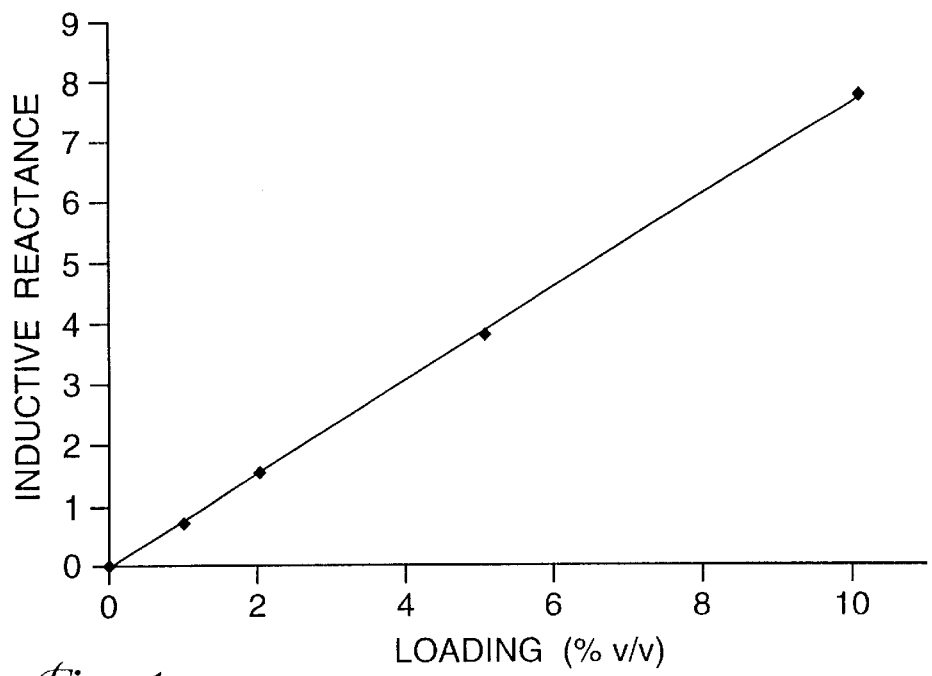
FIG. 1 is a plot of inductive reactance versus loading of coated microparticles in percent volume reaction.

For determining the volume of a polymeric or a pre-polymeric composition, the preferred microparticles have a non-ferromagnetic or non-ferrimagnetic core and a coating that is ferromagnetic, ferrimagnetic, or electrically conductive. For determining the stress level of a polymeric or pre-polymeric composition, the preferred microparticles have a non-ferromagnetic or non-ferrimagnetic core and a coating that is ferromagnetic or ferrimagnetic. Generally, for the above uses, the microparticles can have a variety of shapes, including substantially spherical, elongated, or flat shapes. The shape may be selected to impart desired flow properties to the corresponding admixture given a selected concentration of microparticles in the admixture.

The dimensions of the microparticles can vary, but preferred microparticles have an average major dimension smaller than 1 centimeter and more preferably from 10 micrometers to 1 millimeter. The coating preferably will have an average thickness between about 1 nanometer and 5 micrometers, and more preferably between about 1 and 200 nanometers. The coating can, but need not, cover the entire surface of the core. For example, the coating can form islands on the surface of the core, or the coating material can cover substantially all of the surface. Furthermore, the microparticles can have multiple coatings, partial coatings, or combinations thereof having different metals. Additionally, the microparticles can have one or more non-metallic, inorganic, or organic coatings. Such additional coatings may be used to provide or modify color, stability, particle matrix behavior or abrasivity of the microparticles.

Suitable cores include materials typically used as pigments, reinforcing agents, rheology modifiers, density control agents, or other functional additives in polymeric and pre-polymeric compositions. Examples include glass bubbles, glass beads, glass fibers, fumed silica particles, fused silica particles, mica flakes, single- and multi-component polymeric particles, and combinations thereof. Preferred cores include hollow structures (e.g., in the form of bubbles) to minimize the overall amount of material added to the pre-polymeric or polymeric composition. Preferred core materials are glass microbubbles, e.g., commercially available from Minnesota Mining and Manufacturing Company, Saint Paul, Minn. under the trade name Scotchlite™. Preferred core materials include materials that are already within the compositions of interest so that the coated microparticles can be substituted for the uncoated microparticles in the composition. In this way, the composition can be tagged without requiring reformulation of the composition to obtain the desired rheological properties.

For measuring the volume of polymers or pre-polymeric compositions, the coating for the microparticles generally can be any ferromagnetic, ferrimagnetic, or electrically conductive material that can be coated onto the surface of the microparticle core. A preferred coating should be chemically inert in the relevant compositions under the relevant conditions and stable with respect to degradation and leaching. Suitable ferromagnetic materials include iron, nickel, cobalt, alloys including one or more of these metals, and oxides including one or more of these metals. Appropriate electrically conductive materials include coatable metals, metal alloys, and metal compounds, such as carbides, oxides, nitrides, and silicides. Preferred conductive metals for use in coatings include copper, aluminum, and silver. The preferred material for the coating is stainless steel, which is both electrically conductive and ferromagnetic. If the coating material is ferromagnetic or ferrimagnetic, the core can be an electrically conductive, a non-ferromagnetic, or a non-ferrimagnetic material, in which case the measurements will rely on the ferromagnetic or ferrimagnetic properties of the coating.

For measuring stress levels in polymers, polymeric compositions, or pre-polymeric compositions, the coating for the microparticles generally can be any ferromagnetic, or ferrimagnetic material that can be coated onto the surface of the microparticle core. A preferred coating should be chemically inert in the relevant compositions under the relevant conditions and stable with respect to degradation and leaching. Suitable ferromagnetic materials include iron, nickel, alloys including one or more of these metals or other ferromagnetic metals, and oxides including one or more of these metals. The preferred material for the coating is stainless steel which is ferromagnetic as opposed to non-magnetic stainless steel. If the coating material is ferromagnetic or ferrimagnetic, the core can be an electrically conductive, a non-ferromagnetic, or a non-ferrimagnetic material, in which case the measurements will rely on the ferromagnetic or ferrimagnetic properties of the coating.

A variety of techniques can be used to apply the coating to the core. These techniques include sputtering, vapor deposition, electroless plating, and chemical vapor deposition.

Other useful microparticles for measuring stress levels in polymers, polymeric compositions, or pre-polymeric compositions, including fiber shaped particles having a coating that is magnetic. Typically, the preferred fiber shaped particles have an aspect ratio of 2 or greater and have a diameter of about 15.8 microns. The fiber shaped particles are preferably made of glass. An example of useful glass fibers is Fiberglas™ Milled Glass Fibers 731ED 1/32 inch, commercially available from Owens Corning, Toledo, Ohio.

Useful magnetic materials for use as a coating on the fiber shaped particle include iron, nickel, alloys including one or more of these metals or other ferromagnetic metals, and oxides including one or more of these metals. A preferred coating for fiber shaped particles is stainless steel. Preferably, the coated fibers will have an average coating thickness of between about 1 nanometer and 5 micrometers, and more preferably between about 1 and 200 nanometers.

The microparticles are added to a polymeric or pre-polymeric composition to form an admixture that is a tagged composition. For determining the volume of a composition, the admixture will preferably include between about 0.01 and 50% by volume of the microparticles, and more preferably between about 0.1 and 30% by volume of the microparticles.

For measuring the stress level in a composition, the composition will preferably contain from about 0.01 to about 80% by volume of the microparticles, and more preferably between 0.1 and 30% by volume of the microparticles.

A wide variety of pre-polymeric and polymeric compositions can be used in conjunction with the microparticles. These polymeric or pre-polymeric compositions can be either thermosetting or thermoplastic and can be amorphous or semi-crystalline. Preferably, to determine the stress level in materials, the material will show an elastic-mechanical response, that is, the material will directionally transmit stress. This ability may be dependent upon the frequency of the measurement or the temperature of the material when the measurement is taken.

The methods of the invention are applicable to thermosetting or thermoplastic polymer compositions which are shaped by extrusion, molding, calendering, casting, and other processes into three-dimensional forms. Such shaped forms include films, pipes, fibers, multilayer constructions, laminates, foams, gaskets, wood products, and particle-filled and fiber reinforced composites. Other shaped polymer compositions include those used as vehicle parts, containers, architectural members, paving materials, furniture, bridge members, and other structural elements.

Particularly useful polymer compositions are those that can be incorporated into or with other objects. Such compositions include adhesives, sealants, caulks, gap-filling materials, coatings, conforming wraps and plastisol products.

Preferred polymeric adhesive compositions include crosslinked thermosetting systems such as epoxies (including base-cured epoxies, acid-cured epoxies, and addition-cured epoxies), polyurethanes, silicone resins, acrylate polymers, polysiloxanes, polyorganosiloxanes, and phenolics, as well as blends or hybrids of these types of systems. These same compositions may also be utilized in non-adhesive applications of the methods of the invention.

Useful hot melt adhesives include various polyolefins, polyesters, polyamides, polycarbonates, polyurethanes, polyvinylacetates, higher molecular weight waxes, and related copolymers and blends. Additionally, applicable adhesive compositions would be those which are formed into films and tapes including those which are pressure-sensitive at any point of use.

One suitable class of adhesives includes adhesive compositions such as structural adhesives which include epoxy resins (e.g., derived from diglycidyl ethers of Bisphenol A or novolak resins). Structural adhesives are used in a variety of manufacturing situations including significant use in the automotive industry to bond parts together to reduce the need for welding, to improve so-called noise-vibration-harshness (NVH) characteristics, or to increase the overall stiffness of the part. These materials, which are well-known, are typically prepared by reacting two or more pre-polymeric reagents with each other to form an intermediate "B-stage" resin, which is subsequently further cured to form the final product.

Useful thermoplastic polymeric compositions include polystyrene, polyethylene terephthalate, polymethylmethacrylate, polyethylene, polypropylene, polyvinylacetate, polyamide, polyvinyl chloride, polyacrylonitrile, polyethylene naphthalate, polyether ketone, polysulfone, polycarbonate, and copolymers thereof. Other useful thermoplastics include engineering thermoplastics and thermoplastic elastomers. A thermoplastic composition containing microparticles can be made by generally heating the thermoplastic resin above its melting point or glass transition temperature until a suitable melt viscosity is reached, adding the microparticles, blending, and then allowing the mixture to cool.

The pre-polymeric and polymeric compositions may contain various adjuvants designed to enhance the properties of the resin before or after curing, including reactive and nonreactive diluents, plasticizers, toughening agents, and coupling agents. Other materials which can be added to the composition include thixotropic agents to provide flow control (e.g., fumed silica), pigments, fillers (e.g., talc, calcium carbonate, silica, magnesium, calcium sulfate, beryllium aluminum silicate), clays, glass and ceramic particles (e.g., beads, bubbles, and fibers), and reinforcing materials (e.g., organic and inorganic fibers and granular or spherical particles).

Use

The above-described microparticles can be used in a variety of measurement protocols. One of the measurements that can be made is of the quantity or volume of the composition containing the microparticles. Measuring the electromagnetic properties of the microparticles provides a measure of the number of microparticles. The microparticles can be present in a known concentration within the composition to be measured to provide the quantity determination of the composition. Similarly, the microparticles can be used in a fixed concentration, where the quantity of the composition incorporating the microparticles is determined from a standard curve produced using material with the same fixed concentration.

If the microparticle-containing composition being measured is moving, the measurement will provide information on the flow and, correspondingly, the rate of deposition. If the composition is fixed relative to a substrate or container, the measurements can provide information on the distribution of the composition throughout the substrate or container.

One particularly useful application is in the context of dispensing polymeric or pre-polymeric compositions such as adhesives and pre-adhesive compositions. The material being dispensed can be a single polymeric or pre-polymeric composition that may or may not be later polymerized or crosslinked. This single composition would be used to form the admixture including the microparticles.

Alternatively, the material being dispensed can include two or more polymeric or pre-polymeric compositions that are mixed to form a curable resin, e.g., an intermediate "B-stage" resin. One or more of the components within the curable resin can be combined with a given volume fraction of microparticles. The electromagnetic properties of the microparticles can then be monitored to measure the amount of the reactant(s) dispensed into the reaction mixture. If one of two components is provided with microparticles, the coated microparticles in the reaction mixture can be measured to determine the quantity of reaction mixture. Based on the quantity measurements of the component and the reaction mixture, it can be determined if the two components were mixed in the proper ratio. The level of stress in such curable resins can also be measured as described below.

Alternatively, each component can be mixed with the same or different microparticles. Then, each component can be measured, with or without an additional measurement of the curable resin mixture, to determine whether the components have been mixed together in the correct ratio. Any variation from the desired amount can be noted and/or used to adjust the amount being dispensed. If microparticles with different electromagnetic characteristics, e.g., one ferromagnetic and the other non-ferromagnetic, are placed in the two different components, measurements on the two components being dispensed can determine if the correct component is being dispensed from the particular dispenser.

Another application involves use of the microparticles in the non-destructive testing of articles incorporating a polymeric or pre-polymeric composition. The measurements can be used to determine a variety of properties of the composition within the article, including thickness, integrity, orientation, and continuity. Similarly, a map can be obtained indicating the location of the composition. For example, in the case of structural adhesives forming a bond line to join two parts together, the properties of the bond line can be examined.

Either the electrical or the magnetic properties of the microparticles can be used to make the measurement to determine the volume of the composition containing the microparticles. For example, in the case of ferromagnetic or ferrimagnetic microparticles, magnetic permeability can be measured. Magnetic permeability is a function of the number of ferromagnetic microparticles and the amount of metal coating on the microparticles. Magnetic permeability is defined as the ratio of the total magnetic flux density in a sample to the externally applied magnetic field. Magnetic permeability is a measure of how effective the material is in capturing available magnetic flux, or how magnetic flux due to a coil is multiplied inside a material within that coil. This multiplication directly influences the inductance or inductive reactance associated with the coil.

The magnetic permeability can be measured using an a.c. magnetic hysteresis looper, e.g., a Gerard Electronic MH looper™ operating at a frequency of 10 kHz and an applied field strength of 10 gauss. Typically, the magnetic field is applied with a frequency between 1 and 10 kHz.

Preferably, the inductance can be measured using a solenoid coil containing the sample to be measured connected to a resistance/capacitance/inductance (RCL) meter configured to measure inductance. For maximum sensitivity, the coil and the RCL meter should be optimized for the given measurement parameters. For example, for a 0.9 to 0.5 milliHenry solenoid coil, the inductance due to the sample should be preferably read at least to the nearest 0.01 micro-Henry or better.

Alternatively, inductive reactance can be measured using an eddy current instrument (e.g., a Nortec $19e^{II}$ Eddyscope™, an impedance plane eddy current instrument, equipped with a Nortec OD/100 kHz/A/0.682" probe) to measure the quantity of microparticles (and thus the quantity of pre-polymeric or polymeric composition) within a given volume. With proper calibration the vertical response of the Eddyscope™ is proportional to the inductive reactance; this response is hereinafter referred to as the inductive reactance $(X_L)$. The inductive reactance, i.e., the Eddyscope™ response, is approximately proportional to the loading of the microparticles and coating thickness on the individual microparticles.

Another way of performing the measurement to determine the volume of the composition containing the microparticles is by measuring the dielectric properties of the microparticles. Electrically conductive coatings on the microparticles increase the dielectric constant, which is related to microparticle loading. This can be determined, for example, by measuring the capacitance of a parallel plate capacitor containing the microparticles. An advantage of the dielectric measurement approach over the magnetic permeability approach in certain applications is that the magnetic response is related to the amount of magnetic material coated onto the microparticles, while the dielectric constant is approximately independent of coating thickness. Therefore, much thinner electrically conductive coatings can be used when the dielectric measurements are used.

Other aspects of the electromagnetic properties can be exploited to perform the measurements. For example, certain metals can scatter x-rays sufficiently, so x-ray transmission measurements can be used to quantify the amount of metal-coated microparticles present within a material. Alternatively, coatings can be selected to minimize interference with x-ray transmission so that articles can be examined with x-rays with minimal interference by the coated microparticles.

In addition, microwave or inductive heating methods can be used to heat the microparticles, after which the associated infrared emissions can be measured to quantify the amount of microparticles (and thus the amount of polymeric or pre-polymeric composition).

Another application of the invention involves the use of the microparticles in determining or measuring the level of stress in polymers or pre-polymeric compositions. Generally, the magnetic properties of the particular microparticles present in the compositions are measured and correlated to the level of stress in the composition containing the microparticles. Such polymers or polymer compositions containing magnetic microparticles may generally be made as described hereinbefore.

Generally, the correlation is obtained by measuring the magnetic property or characteristic of samples whose stress condition is known or for which the stress condition can be correlated with other useful parameters. The level of stress in the polymeric material can be used, for example, to determine the degree of cure of an adhesive or other thermosettable or crosslinkable polymeric material, the level of external forces applied to a polymer composition or substrate, the amount or quality of adhesion of an adhesive to a substrate, and thermal history of the polymer from heating and cooling cycles.

A particularly useful magnetic property of the magnetic particles for measuring stress levels in polymeric compositions is the magnetic permeability. The magnetic permeability of the microparticle changes with stress applied to the microparticle. The change in the magnetic permeability of a magnetic material with an applied stress is commonly referred to as "inverse magnetostriction" and is also known as the "magnetomechanical" effect. The measured changes in the magnetic permeability of the microparticles can then be correlated with the amount or level of stress within the composition containing the microparticles. Increases or decreases in the stress in the composition are measured as changes in the magnetic permeability of the magnetic particles. The amount of stress in the polymer is directly proportional to the amount of change in the magnetic permeability of the particles measured. Applicants have discovered that these effects are generally much larger for coated magnetic particles than for particles entirely composed of magnetic material.

To determine the stress level in polymers or polymeric compositions containing magnetic particles, a parameter is measured that is directly related to the magnetic permeability of the magnetic particles. Such parameters can be the inductance of a solenoid coil or the inductive reactance of an eddy current probe as described above, with both measurements taken in the vicinity of the sample. As much of the sampling volume as possible should contain the sample to be measured for optimum sensitivity. For example, the sample can be contained within the solenoid coil. Typically, the stress level of a particular composition is calibrated to these parameters for stressed versus unstressed polymer samples.

Preferably, the change in the magnetic permeability of the magnetic particles for measuring the stress level in polymers is monitored using a coil connected to an RCL meter. As described above for measuring the volume of a polymeric composition, for maximum sensitivity, the coil and the RCL meter should be optimized for the given measurement parameters.

If the measurement of the magnetic characteristic of a particular magnetic particle is performed over time in which the external temperature may change, then preferably, the measurement is corrected for the effect of temperature variations on the performance of the particular instrument used to measure the magnetic characteristic. The temperature variations are typically due to the surrounding environment in which the measurements are being made.

Generally, the temperature corrections are performed by subjecting the probe or instrument to different temperatures and recording the performance of the instrument at that temperature. The correlation of temperature to performance is then used to correct the measurement of the samples being characterized. For example, a solenoid coil can be placed in an oven set to various temperatures and its inductance determined at each temperature.

The temperature-corrected inductance (where the contribution to the inductance from the empty solenoid coil is eliminated) is determined by measuring the temperature of the solenoid coil, determining the inductance of the empty solenoid coil associated with that temperature, and then subtracting that inductance from the inductance of the solenoid coil (measured at the same temperature) containing the sample. This can be done automatically by using a computer which can also be used to carry out real time averaging of the resulting data.

One particularly useful application of measuring the stress level in polymeric compositions or polymers containing magnetic particles is for determining the degree of cure of an adhesive composition. As the adhesive cures, the internal stress levels of the adhesive usually increase. For example, the progress of cure of a polymer or an adhesive can be followed in real time by monitoring inductance. In this case, the stabilization of the inductance indicates that the crosslinking of the adhesive has progressed substantially to the degree possible at a given temperature. Of course, to determine the degree of cure of a polymer at any particular time, an independent measurement of the degree of cure at that time can be performed to create a standard curve. Degree of cure of the adhesive composition could be determined for example, by comparison of the heats of reaction of uncured, partially cured and substantially cured polymeric material.

Alternatively, this measurement can be performed to detect problems related to incomplete cure of the adhesive. Additionally, in an adhesive dispensing system, this method can be used to detect undesired or premature cure of the polymer.

The methods of the invention can also be used to determine the cure of an adhesive which is subjected to induction heating or some other process meant to accelerate the cure rate of the adhesive. Accordingly, a useful paramenter to which inductance changes can be related is the change in bond strength of an adhesive realized in, for example, an overlap shear bond mode with an adhesive whose cure is being monitored. Such a parameter is relevant to the development of handling strength in structural parts.

Another useful application of measuring the level of stress in polymers or polymeric compositions is to determine the magnitude of external forces applied to the polymer or polymeric composition, for example, compression or tensile forces. The external forces can be static or dynamic and can be mechanical, vibrational, or acoustical. The external forces applied on a particular sample containing magnetic microparticles can be measured by correlating the indicated stress level, monitored by a suitable parameter, to a standard curve for that particular sample system. In this way, the method of the invention can be used to predict the performance of adhesives subjected to such external forces.

Another application of the methods of the invention involves the use of the microparticles in acoustic attenuating materials. Examples of such attenuating materials are described in detail in U.S. Pat. No. 5,504,281, incorporated by reference herein. Such materials use glass bubbles at a high volume loading in a starved epoxy matrix. Such material is efficient in attenuating incident sound either by absorption or by reflection. Such materials can also be improved by the addition of magnetic particles to assist in the characterization of the acoustic environment. For example, an inductive sensor head placed in the vicinity of the acoustic attenuating structure could be used to determine the acoustically generated stress distributions, thus enabling adjustment for this environment to be carried out.

Another application of measuring the stress levels in polymers or polymeric compositions is to determine the amount of or quality of adhesion of an adhesive material to substrate. For example, the magnetic characteristics of adhesive systems containing magnetic particles could be correlated with a particular adhesive bonding characteristic. The determination of adhesion will vary depending on the object of determination. For example, if the object is the determination of the bond strength of an adhesive to a substrate, a correlation can be established between inductance and bond strength. This correlation can be made because in many instances, bond strength is a function of crosslink density or degree of cure, which are both influenced by for example, reactants and time and temperature of cure. As another example, if the object is the determination of the quality of adhesion of an adhesive to a substrate, which can be related to failure mode in the event an adhesion test is performed, changes in the inductance of the sample can indicate the intimacy of contact between the adhesive material and the substrate.

Yet another application for the methods of the invention is to determine resultant stresses as a result of heating and cooling the polymer. This application can also be used to indicate performance characteristics of the polymer. For example, different quenching or cooling rates will produce different levels of stress in a polymeric system. Thus, the methods of the invention can be used to monitor the thermal history of polymeric materials.

Another application involves the use of microparticles in nondestructive testing to determine the direction of the stress in a polymer or polymeric composition. The direction of the stress in a polymer composition can influence its physical properties, for example, strength and resiliency. For example, when fiber shaped particles having a particular magnetic coating are dispersed throughout the polymer in a known orientation, stress applied parallel to the fiber axis produces a different and unique change in magnetic permeability than when a stress is applied perpendicular to the fiber axis. In knowing the orientation of the fibers and the resulting change in the magnetic characteristic of the fiber when subjected to a known directional stress, the direction of the stress in the substrate may be correlated to a particular change in the measured magnetic characteristic. This correlation can then be used to determine the direction of stress in other substrates that contain the particular coated fiber shaped particle.

The invention will now be described by way of the following non-limiting examples.

EXAMPLES

Example 1

This example demonstrates that glass bubbles can be coated with a very thin magnetic stainless steel coating.

K37 Scotchlite™ glass bubbles (sold by Minnesota Mining and Manufacturing Company, Saint Paul, Minn.) were sputter coated with 304 stainless steel according to the procedure described generally in U.S. Pat. No. 4,618,525, incorporated herein by reference. In this specific case, a 304 stainless steel target was dc magnetron sputtered for 7.0 hours at 8.0 kW at an argon sputtering gas pressure of 5 millitorr onto 415 grams of K37 Scotchlite™ glass bubbles. The 304 stainless steel sputter target was non-magnetic austenitic face centered cubic, but deposits as the magnetic ferritic body centered cubic form. These materials have been described in a publication by T. W. Barbee, B. E. Jacobson and D. L. Keith, 63, *Thin Solid Films* 143–150 (1979).

The resulting stainless steel coated bubbles had an iron content of 7.86% by weight (determined by inductively coupled plasma emission spectroscopy), corresponding to 11.2% by weight stainless steel (which is 70% by weight iron). A typical 304 stainless steel composition is 70% iron, 19% chromium, 10% nickel, and 1% manganese. The surface area of the glass bubbles was determined by the B.E.T. method to be 0.55 square meters per gram. The density of the coated bubbles was measured using a Beckman Model 930 air comparison pycnometer. The density of the uncoated bubbles was 0.36 g/cc, and that of the coated bubbles was 0.41 g/cc.

The metal coating thickness can be calculated from the relevant relationship described in U.S. Pat. No. 5,409,968. In this case, the coating thickness was determined to be 29 nm.

Example 2

This example demonstrates the effect of volume loading of stainless steel coated bubbles on inductive reactance.

Glass bubbles with a 29 nm thick stainless steel coating were used. Devcon™ 5-minute epoxy (ITW Devcon™, Danvers, Mass.) was used to prepare samples with various volume loadings of coated bubbles. This mixture was placed in 80 mm long Pyrex™ glass tubes with 13.2 mm inner diameter and a 16.0 mm outer diameter.

The inductive reactance was then measured using a Nortec Eddyscope™. Several variables can be optimized on the Eddyscope™. For a given probe, these are (1) frequency, (2) gain, and (3) probe drive voltage. The rotation ("Rot" knob on the instrument) was used to calibrate the Eddyscope™ so that displacement along the y-axis provided a measure of inductive reactance. Inductive reactance in unscaled units was read from the Eddyscope™ display. Barium ferrite, which is magnetic but not significantly electrically conductive, was chosen as a calibrating material. With a frequency fixed at 100 kHz, rotation was varied until introduction of the barium ferrite sample resulted in a purely vertical response on the Eddyscope™ screen (rotation=311 degrees).

The Eddyscope™ settings included a gain of 76.0 dB with probe drive of "Mid." Reactance versus microparticle loading is plotted in FIG. 1. This illustrates the linear relationship between the two variables. It shows that the reactance can be used as a good measure of the bubble content.

Example 3

This example demonstrates the effect of coating thickness on inductive reactance.

Procedures similar to that in Example 1 were carried out to make stainless steel coated glass bubbles with coating thicknesses of 59 and 86 nanometers. The density for each of the coated bubble samples was 0.44 and 0.49 g/cc, respectively. In addition, glass bubbles with a 29 nm thick stainless steel coating prepared as in Example 1 were used.

Figure 2:
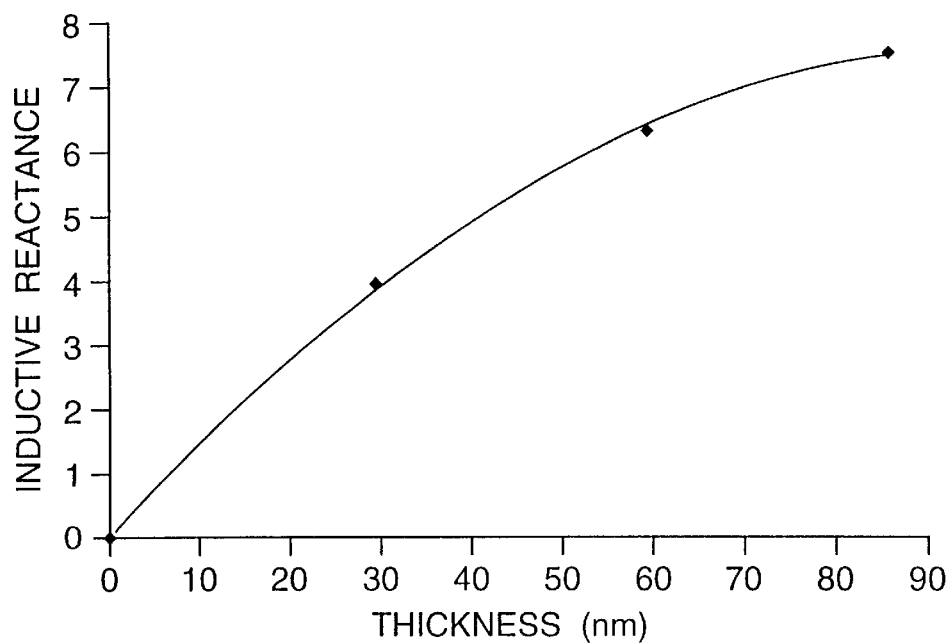
FIG. 2 is a plot of inductive reactance versus coating thickness of the incorporated coated microparticles.

The Eddyscope™ parameters were set as in Example 2 except that the gain was 70.0 dB. Test samples in Devcon™ 5-minute epoxy were prepared at 10% volume loading for each of the three samples of coated bubbles. The inductive reactance was measured and is plotted as a function of the stainless steel coating thickness in FIG. 2. The inductive reactance increases monotonically with stainless steel thickness.

Example 4

In this example, the use of acicular particles is demonstrated.

Milled glass fibers (Type 731 DD 1/16 inch milled glass fibers) were obtained from Owens/Corning Corporation (Toledo, Ohio). They had an aspect ratio range of approximately 1 to 40, with a fiber diameter of 15.8 microns. Stainless steel was deposited onto 1570 grams of these fibers for 20 hours at 8.0 kW in the manner previously described in Example 1.

The weight percent iron was determined to be 6.2%, corresponding to 8.9% by weight stainless steel. The surface area of the uncoated fibers was 0.10 square meters per gram.

The stainless steel coated milled glass fibers were dispersed in Devcon™ 5-minute epoxy at a volume loading of 10%. The mixture was placed in glass tubes, as described in Example 2. The Eddyscope™ was set to a gain of 68.0 dB with Probe Drive on High. The inductive reactance was determined to be 8.9.

Example 5

In this example, the use of a magnetic cobalt coating is demonstrated.

Milled glass fibers were sputter coated with cobalt, as described in Example 1, using a MAK 3 inch Magnetron Sputtering Source (US Thin Film Products Inc., Campbell, Calif.). The weight percent cobalt was determined to be 5.6%, corresponding to a coating thickness on the fibers of 67 nm.

The cobalt coated milled glass fibers were dispersed at 10% by volume in Devcon™ 5 minute epoxy and loaded into a glass tube as described in Example 4. The Eddyscope™ was set to the same conditions as Example 4 except that the gain was raised to a value of 80.0 dB. The inductive reactance was determined to be 9.6.

Example 6

In this example, flat, flake shaped particles were used. Silicone rubber, rather than epoxy, was the polymer component. Stainless steel was deposited onto 460 grams of 200HK Suzorite™ mica flakes (Suzorite Mica, Inc., Hunt Valley, Md.) for 13.5 hours at a power of 8.0 kW in the manner described in Example 1.

The stainless steel-coated mica flakes were dispersed at a volume loading of 10% into RTV 615™, a silicone rubber available from Dow Corning Corporation, Midland, Mich. This was loaded into a glass tube as described in Example 3. The Eddyscope™ was set to the same conditions as Example 4 except that the gain was set to a value of 60.0. The inductive reactance was determined to be 8.4.

Example 7

This example illustrates the relationship between the measured magnetic permeability and the stainless steel coating thickness on the glass bubbles.

The three stainless steel-coated bubble samples described in Example 3 were combined with Devcon™ 5 minute epoxy at a volume loading of 10%. The material was used to fill tubes (straws) with a 5 mm internal diameter to a depth of 70 mm. The permeability was determined from a hysteresis loop obtained using a Gerard Electronic MH looper operating at a frequency of 10 kHz and an applied field strength of 10 gauss. The permeability was calculated from the maximum applied field in gauss and the maximum magnetization in emu/cc. A BH looper could also be used.

Figure 3:
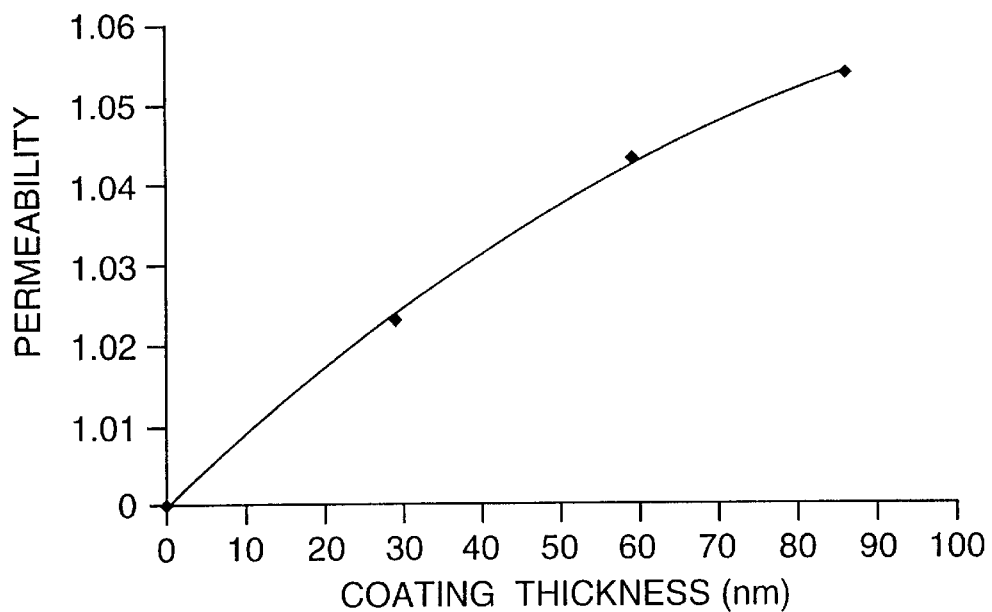
FIG. 3 is a plot of permeability versus coating thickness of the incorporated coated microparticles.

The permeability is plotted versus stainless steel coating thickness in FIG. 3. Permeability is seen to monotonically increase with coating thickness. This demonstrates that these very thin magnetic coatings can provide significant and reproducible permeabilities. The higher coating thicknesses give higher permeabilities.

Example 8

Figure 4:
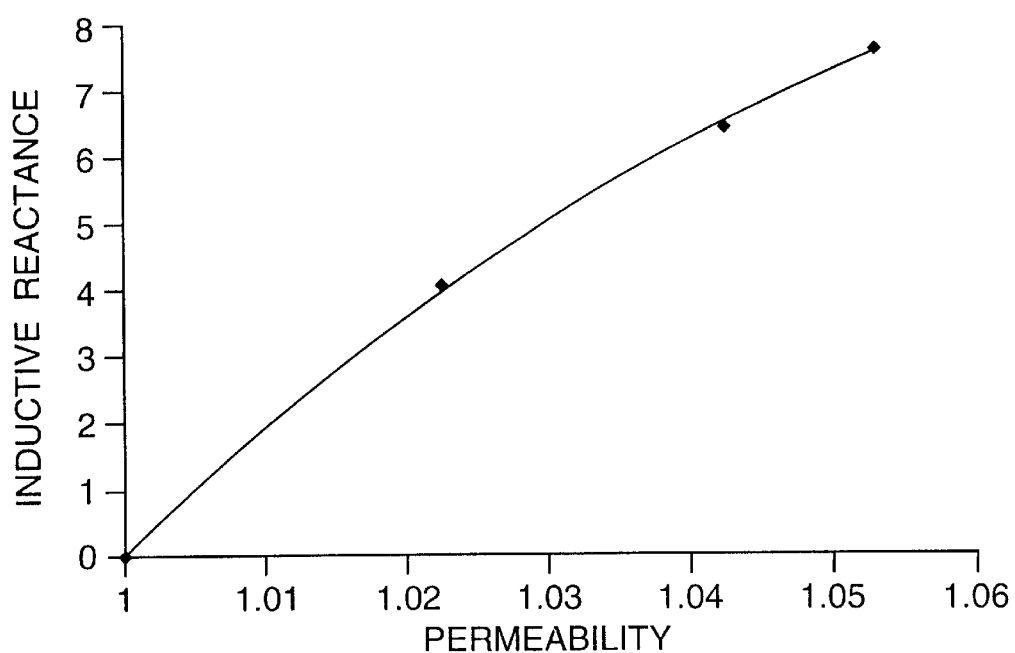
FIG. 4 is a plot of inductive reactance versus permeability.

This example demonstrates that the inductive reactance for coated particles is directly related to their magnetic permeability. Magnetic permeability is a fundamental magnetic property of the coated microparticles incorporated into an adhesive. Magnetic permeability is related to the Eddyscope™ response, which is the inductive reactance. To demonstrate this relationship, the magnetic permeability measurements of Example 7 are plotted in FIG. 4 against the inductive reactance measurements of Example 3 using the same coating thicknesses of stainless steel on glass bubbles. The inductive reactance is monotonic, and almost proportional to the permeability.

Example 9

This example demonstrates the use of the magnetic coated microparticles within an adhesive for non-destructive testing. This could be used as a form of non-destructive testing to determine the continuity of the adhesive bondline.

Devcon™ 5 minute epoxy was used to make an adhesive having a 26% volume loading of glass bubbles with a 29 nm thick stainless steel coating prepared as in Example 1. About 1% by volume of 60–100 micron diameter glass beads were added as spacers. A bead of this material was laid onto a strip of aluminum measuring 0.61 mm thick, 19 mm wide, and 31 cm long. In the middle, the adhesive was removed from a span of about 3 cm. An identical piece of aluminum was pressed onto the adhesive on the first piece to make an aluminum-epoxy-aluminum sandwich structure. Adhesive which exuded from both edges of the structure was removed after the adhesive had cured.

Figure 5:
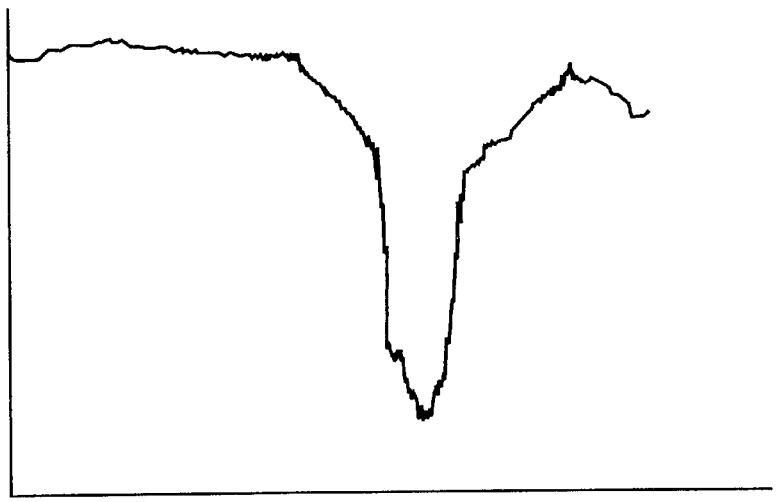
FIG. 5 is an Eddyscope™ scan of an aluminum-epoxy-aluminum structure.

A Nortec SPO-5781™ 1 kHz-50 kHz edge probe was used to scan the structure. The Eddyscope™ was set at 5 kHz with 0 degrees rotation and probe drive Hi. The scan is presented as a screen print in FIG. 5. The gap in the adhesive between the two aluminum pieces is clearly shown.

Example 10

This example demonstrates the use of a simple solenoid coil in place of an eddy current instrument, such as an Eddyscope™, to determine loading of coated microbubbles.

A solenoid coil was prepared by winding size 36 (0.127 mm diameter) insulated copper wire onto a 19.0 mm o.d. glass tube. The coil had 333 turns in four layers over a length of 3.0 cm. The two leads from the coil were connected to a Tenmark 72-370™ digital LCR meter. This LCR meter was a hand-held device capable of measuring inductance, capacitance, or resistance when attached to an appropriate sensing device. Eighty mm long, 16.0 mm outer diameter glass tubes containing Devcon™ epoxy with various loadings of glass bubbles provided with 29 nm thick stainless steel coatings were inserted into a tube (centered in the coil region), which had a 16.5 mm inner diameter.

Figure 6:
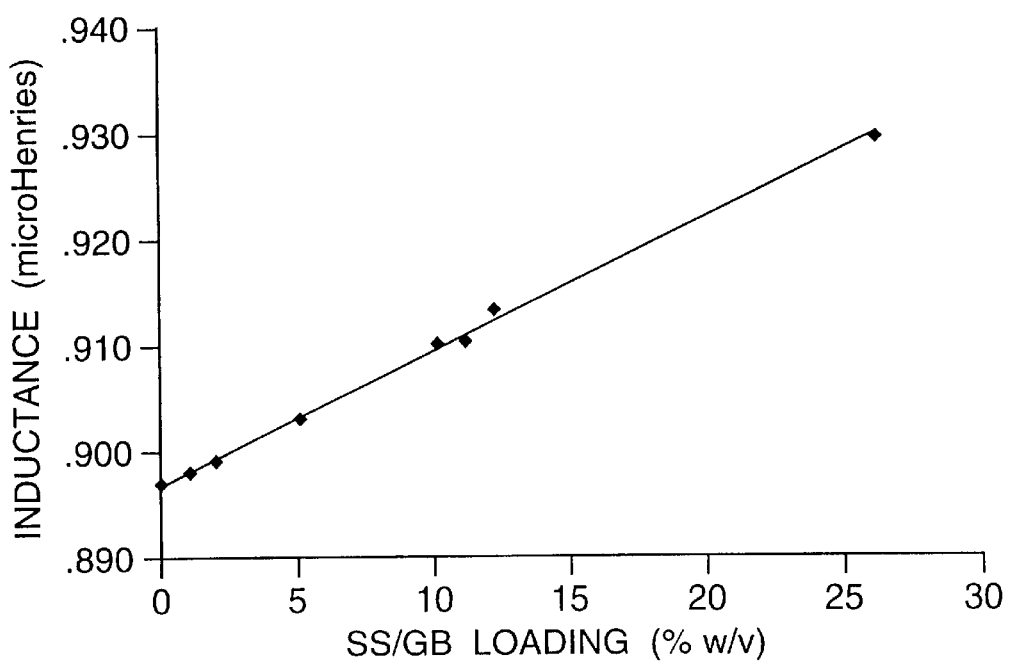
FIG. 6 is a plot of inductance versus coated microparticle loading in percent volume fraction.

The inductance was read off the LCR meter and is plotted versus volume loading in FIG. 6. The approximate linear relationship between inductance and loading demonstrates the fundamental relationship between the two. This also shows that equipment other than an eddy current instrument can be used in sensing loadings in the adhesives containing the microparticles.

Example 11

This example demonstrates that capacitive, rather than inductive, measurements can be used to determine microparticle loading in adhesives.

A two-plate capacitor was made for detecting the capacitance of an adhesive material. Two pieces of adhesive-backed copper foil were cut to form rectangles 2.0 cm wide×3.0 cm long. These were affixed to the outside of a glass tube of the same dimensions as the larger glass tube in Example 10. They were affixed opposing one another so as to form a curved-plate rather than parallel-plate capacitor. Electrical leads from each plate were connected to the same LCR meter described in Example 10. This sensing apparatus was loaded with various samples of adhesives containing coated microparticles as described in Example 10.

Figure 7:
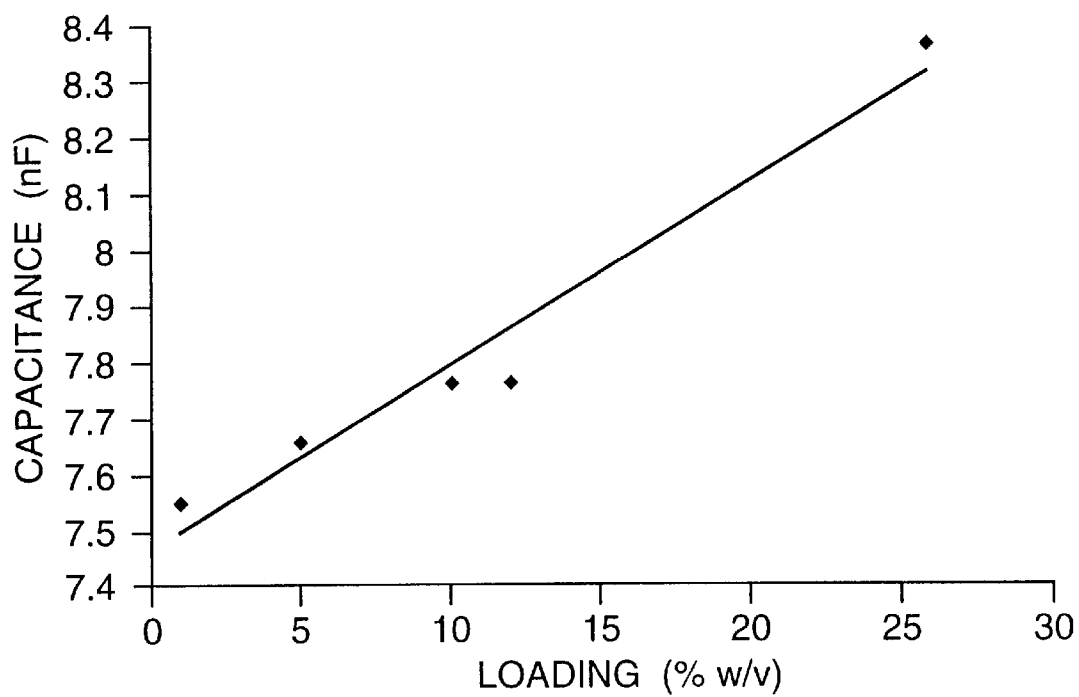
FIG. 7 is a plot of capacitance versus coated microparticle loading in percent volume fraction.

The capacitance was read off the LCR meter and is plotted versus loading of the coated microparticles in the adhesive in FIG. 7. The approximate linear relationship between the two demonstrates that measurement of capacitance provides another means of determining concentration.

Example 12

This example demonstrates the ability of an object made with a material incorporating microparticles to be mapped using an Eddyscope™. It also demonstrates the use of a thermoplastic, rather than thermoset, resin.

A rectangular plastic tray was obtained from Minnesota Mining and Manufacturing Company, St. Paul, Minn. It is identified as Thin PQFP™ 132 21002-203. It is 32.3 cm wide by 0.85 cm thick. It contains 24% by volume stainless steel-coated milled glass fibers dispersed in Mindel S1000, a thermoplastic resin obtained from Amoco Chemical Company, Chicago, Ill. A Nortec S-300™ Hz-10 kHz/0.62 surface probe was oriented vertically 1 mm above the surface of the tray in such a manner as to allow the tray to be scanned under it. The Eddyscope™ was set with a frequency of 1.0 kHz, a gain of 90 dB, a probe drive "Hi," and rotation 18 degrees. The tray was manually scanned under the probe with inductive reactance versus time being recorded.

Figure 8:
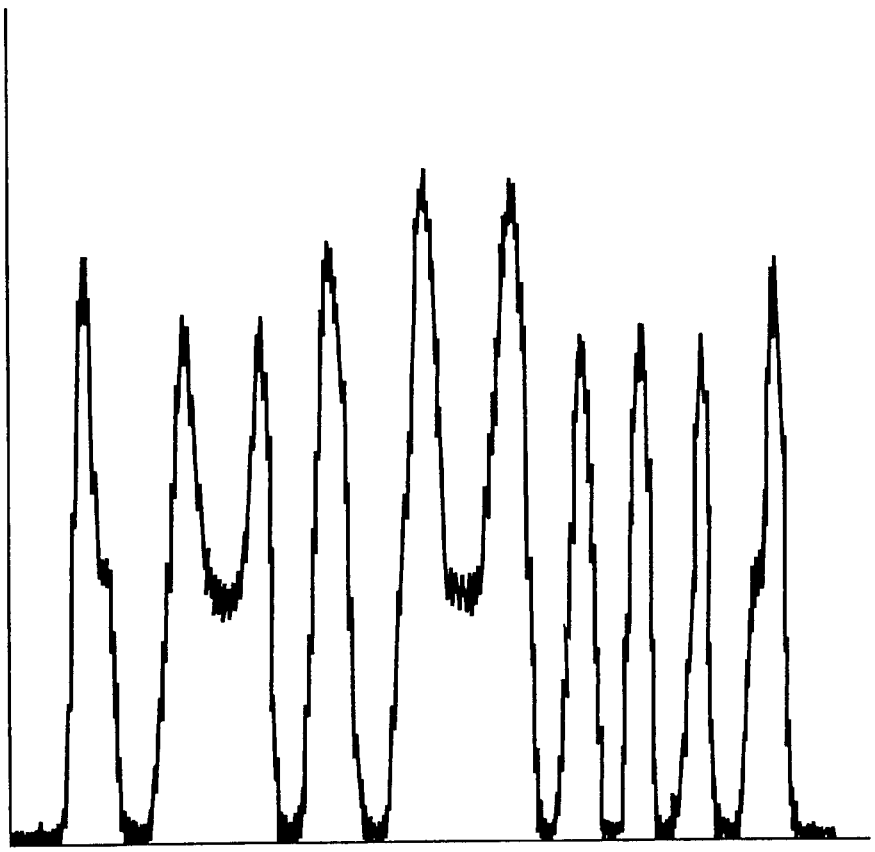
FIG. 8 is an Eddyscope™ scan of a thermoplastic tray containing coated microparticles.
Figure 9:
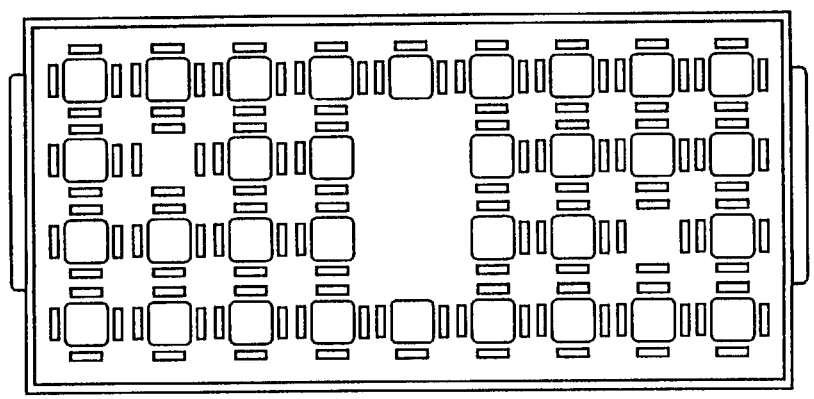
FIG. 9 is a physical map of the tray of FIG. 8 made using the Eddyscope™ readings.

The scan (FIG. 8) shows a map of the presence of high spots and voids in the tray. A physical map of the tray from the top side is also given here for comparison in FIG. 9. The scan was made in a straight line from one end of the tray to the other on the second row from the top, as indicated by the horizontal arrow.

Example 13

This example demonstrates the ability of a material incorporating microparticles to be mapped using capacitance, rather than an Eddyscope™.

A parallel-plate capacitor was set up for the purpose of scanning the tray of Example 12. The top electrode was a rectangle measuring 1.4 cm by 1.0 cm and the bottom electrode measured 15 cm by 15 cm. The spacing between the electrodes was 0.8 cm. The capacitance was measured using the meter described in

Example 10.

Figure 10:
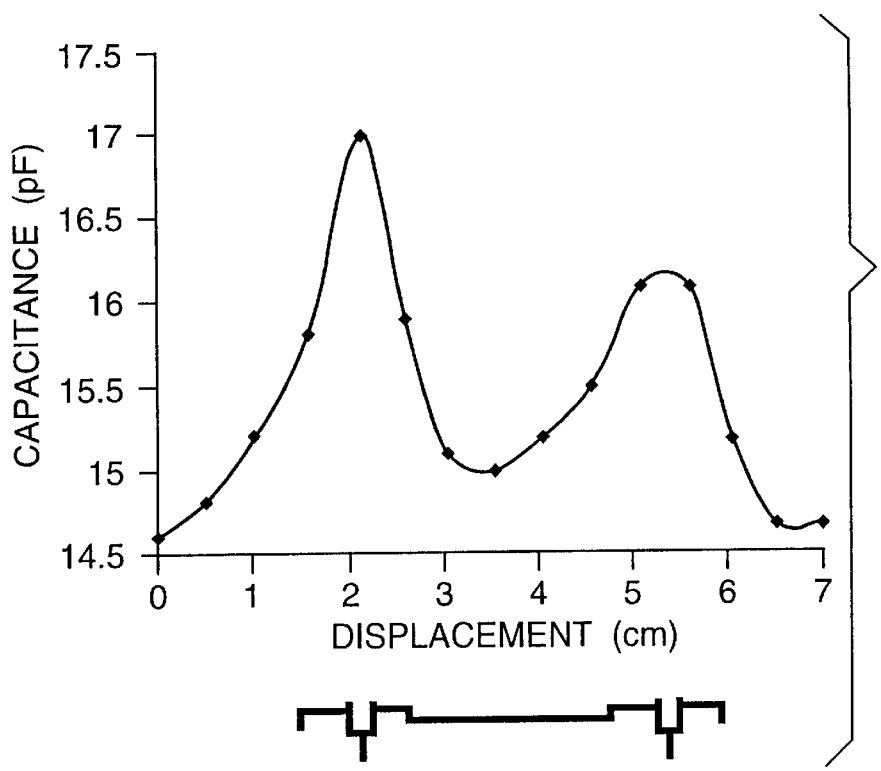
FIG. 10 is a plot of capacitance versus displacement along a width of the tray of FIG. 8 with a schematic of the cross section of the tray shown below the plot.

The tray was moved through the sensing capacitor, with the capacitance recorded at 0.5 cm increments. The capacitance map is shown in FIG. 10 along with a schematic cross section of the tray. The voids, peaks, and valleys on the surface of the tray are clearly indicated in this scan (within the resolution of the top electrode).

Example 14

This example demonstrates how an off-ratio mixing event can be detected when the adhesive contains coated glass bubbles. The following two component adhesive formulation was prepared using glass bubbles with a 29 nm stainless steel coating:

|  | Parts (g) | Density (g/cc) | Volume |
|---|---|---|---|
| Part B |  |  |  |
| Epon 828 DGEBA | 80 | 1.17 | 68.38 |
| Heloxy 107 epoxy diluent | 20 | 1.09 | 18.35 |
| TS-720 fumed silica | 2 | 1.8 | 1.11 |
| 0.25-mm glass beads | 3 | 2.5 | 1.20 |
| GP-71 fused silica | 20 | 2.2 | 9.09 |
| 29 nm SS-coated glass bubbles | 21.7 | 0.41 | 52.93 |
| Totals | 146.7 |  | 151.05 |
| Part A |  |  |  |
| Polyamidoamine | 40 | 1.0 | 40.00 |
| H221 amine | 6 | 0.98 | 6.12 |
| Aricamine ™ K54 tertiary amine | 8 | 0.97 | 8.25 |
| ATBN 1300x16 liquid rubber | 10 | 0.96 | 10.42 |
| TS-720 fumed silica | 3 | 1.8 | 1.67 |
| GP-71 fused silica | 20 | 2.2 | 9.09 |
| Totals | 87 |  | 75.54 |

Epon 828™ is a diglycidyl ether of bisphenol A available from Shell Chemical Company, Houston, Tex. Heloxy 107 is a diglycidyl ether of cyclohexane available from Shell Chemical Company, Houston, Tex. TS-720 is a hydrophobic fumed silica available from Cabot Corporation, Aurora, Ill. The glass beads have a nominal diameter of 0.01 inches, available from Cataphote, Inc., Jackson, Miss. GP-71™ is an amorphous silicon dioxide available from Harbison-Walker Corporation, Pittsburgh, Pa. The glass bubbles are hollow glass microspheres available from Minnesota Mining and Manufacturing Company, St. Paul, Minn. The polyamidoamine is an amine-terminated polyamide. H221 is 4,7,10-trioxatridecane 1, 3-diamine available from BASF, Parsippany, N.J. Ancamine™ K54 is 2, 4, 6-trimethyaminomethyl phenol available from Air Products and Chemicals, Inc., Allentown, Pa. ATBN 1300x16 is acrylonitrile-terminated butadiene liquid rubber available from B. F. Goodrich Company, Cleveland, Ohio.

The proper mix ratio of this adhesive by weight is 146.7/87 or 1.69 B:A, obtained by dividing the formula weight of Part B by the formula weight of Part A. (By volume, by a similar procedure, the volume mix ratio is 151.05/75.54 or 2.0 B:A). By increasing or decreasing 1.69 by 10%, it can be determined that a B:A mix ratio of 1.86:1.00 represents a plus 10% off-ratio while 1.52:1.00 represents a minus 10% off-ratio.

Mixtures of the above Part B and Part A were prepared at B:A by weight mix ratios of 1.52:1.00, 1.69:1.00, and 1.86:1.00; degassed while being mixed; and pulled by vacuum into three separate half-inch static mixing nozzles. After being filled, the nozzles were inserted into the eddy current probe as described in Example 2.

The response of the Eddyscope™ was somewhat more consistent when the mixing elements were removed from the static mix nozzles because filling of the nozzles is more uniform without the mixing elements. In a dynamic situation where many gallons of mixing adhesive are pumping through a given nozzle, a steady-state response could be achieved.

Figure 11:
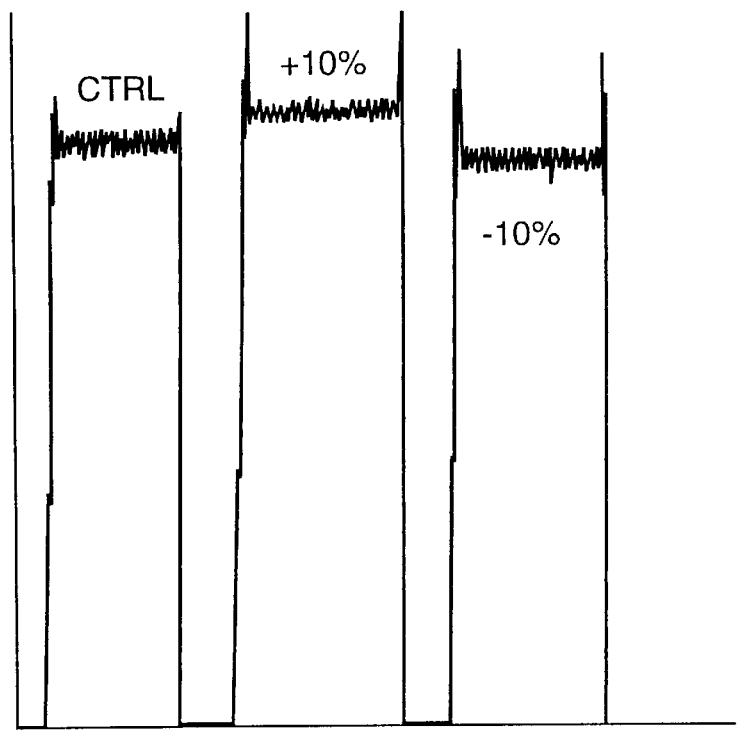
FIG. 11 is an Eddyscope™ scan indicating the different reading obtained with different ratios of one component of an adhesive mixed with a second component of an adhesive wherein one component contains microparticles.

To simulate this dynamic response, the nozzle is moved back and forth in the probe. As FIG. 11 demonstrates, the Eddyscope™ responses corresponding to adhesives mixed under the proper (control) mix ratio, −10% off-ratio, and +10% off-ratio are readily differentiated from each other. The measured responses can provide a process window within which mix ratio can be established and maintained using an adhesive containing coated glass bubbles.

Example 15

This example demonstrates the substitution of varying amounts of coated glass bubbles for already present plain glass bubbles.

A two component adhesive (16-1) was made using uncoated glass bubbles, and corresponding versions were made (16-2 through 16-6) by substituting for some or all of the plain glass bubbles in the B adhesive component with stainless steel coated glass bubbles having a 29 nm stainless steel coating. The B adhesive component contained a 0.35 volume fraction of glass bubbles.

|  | Parts by Weight (g) in B Component | | | | | |
| --- | --- | --- | --- | --- | --- | --- |
|  | 16-1 | 16-2 | 16-3 | 16-4 | 16-5 | 16-6 |
| Epon 828 DGEBA | 80 | 80 | 80 | 80 | 80 | 80 |
| Heloxy 107 epoxy diluent | 20 | 20 | 20 | 20 | 20 | 20 |
| TS-720 fumed silica | 2 | 2 | 2 | 2 | 2 | 2 |
| 0.25-mm glass beads | 3 | 3 | 3 | 3 | 3 | 3 |
| GP-71 fused silica | 20 | 20 | 20 | 20 | 20 | 20 |
| K37 glass bubbles | 19.6 | 19.4 | 18.6 | 17.6 | 9.8 | 0 |
| SS-coated bubbles (29 nm coating) | 0 | 0.2 | 1.1 | 2.2 | 10.9 | 21.7 |
| Total formula weight (g) | 144.6 | 144.6 | 144.7 | 144.8 | 145.7 | 146.7 |
| B:A by Weight | 1.66:1 | 1.66:1 | 1.66:1 | 1.66:1 | 1.67:1 | 1.69:1 |
| B:A by Volume | 2:1 | 2:1 | 2:1 | 2:1 | 2:1 | 2:1 |
| Total Volume Fraction Bubbles on B Side | 0.35 | 0.35 | 0.35 | 0.35 | 0.35 | 0.35 |
| Volume Fraction of Coated Bubbles | 0.0 | 0.0035 | 0.0175 | 0.035 | 0.175 | 0.35 |
| Substitution Level Based on Total Bubble Volume (percent) | 0 | 1 | 5 | 10 | 50 | 100 |

Part A is as given below and is used in the given mix ratio with each of the above Part Bs to form a 2:1 mixture by volume. The nature of the ingredients of the A and B compositions are described further in Example 14.

| Part A | |
| --- | --- |
| Polyamidoamine | 40 |
| H221 amine | 6 |
| Ancamine ™ K54 Tertiary Amino | 8 |
| ATBN 1300 × 16 Liquid Rubber | 10 |
| TS-720 Fumed Silica | 3 |
| GP-71 Fused Silica | 20 |
| Totals | 87 |

The volume fraction of total glass bubbles was kept as close as possible to a constant value for all B components using calculations involving the 0.37 g/cc density of the uncoated glass bubbles and the 0.41 g/cc density of the stainless steel coated glass bubbles. The parts of all bubble components were rounded to the nearest 0.1 g.

Using the listed mix ratios and a multiplication factor of 30, samples of the B components 16-1 through 16-6 were mixed under vacuum with the appropriate amount of the A component and deposited into flat-bottomed plastic weighing dishes. The component mixtures were allowed to cure at room temperature into a solid mass about 2.5 inches in diameter and at least 0.5 inches thick. After cure, the dish was peeled off of each hardened adhesive to present a flat surface which was interrogated using a flat surface probe, Nortec #954769, S/1 kHz-50 kHz/0.31. The Eddyscope™ was set at a frequency of 50 kHz, a gain of 67.0, and a rotation of 64 degrees.

Figure 12:
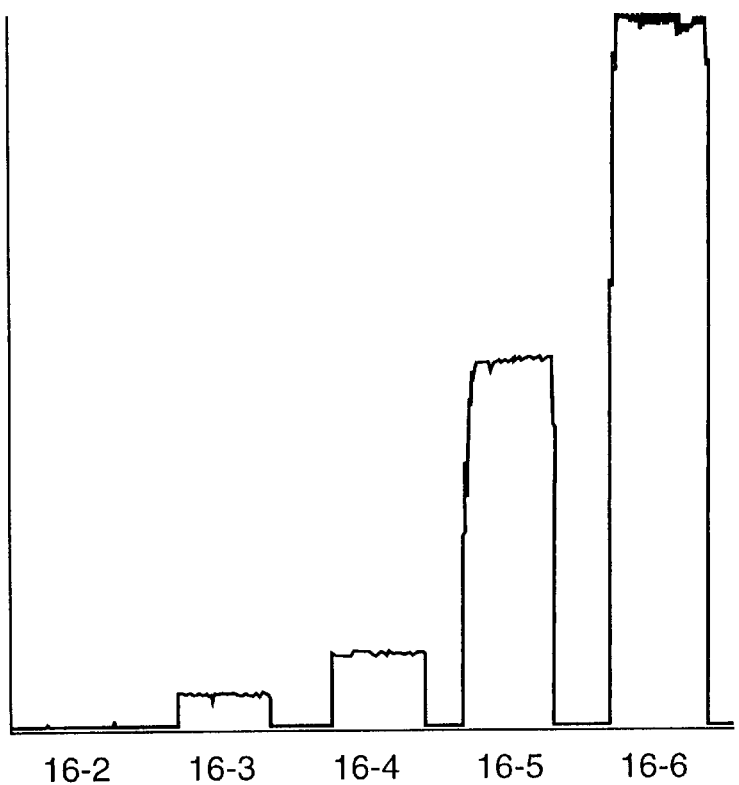
FIG. 12 is an Eddyscope™ scan indicating the different readings obtained from a volume of composition containing various loadings of coated microparticles.

Nulling in air and setting the surface probe against the flat bottoms of each of the molded samples containing coated glass bubbles in turn produced the results shown in FIG. 12. (The signal for the 16-2 material is weak due to the desire to fit data for all samples on the same screen/chart but could be increased by setting gain higher than 67.0.) The data clearly shows the systematic fashion in which the signal increases with increasing substitution of coated bubbles for uncoated bubbles with, for example, the signal for 10% substitution being approximately twice that for 5%, the signal for 50% being approximately five times that for 10%, and so on. The sample made using 16-1 mixed with Part A gave no measurable Eddyscope™ response.

Example 16

This example demonstrates the direct detection of compressive stress on a polymer.

A 0.6 milliHenry solenoid coil was prepared by winding size 36 (0.127 mm diameter) insulated copper wire onto a 19.1 mm o.d. glass tube. The coil had a total of 200 turns in two layers over a length of 16.1 mm. The two leads from the coil were connected to a Fluke™ PM6306 RCL meter configured to read inductance. The sensitivity was such that the inductance could be read to the nearest 0.01 microHenry. An RCL meter is a device which directly measures inductance. The frequency was set at 20 kHz and the potential was set on "high." The measured inductance for the empty coil was 607.77 microHenry.

K37 Scotchlite™ glass bubbles (sold by Minnesota Mining and Manufacturing Company, Saint Paul, Minn.) were sputter coated with stainless steel in a manner similar to that described in Example 1. In this example, the thickness of the coating on the microbubbles was determined to be 23 nm.

The stainless steel coated bubbles were mixed into Devcon™ 5-minute epoxy (ITW Devcon™, Danvers, Mass.) at a level of 13% by volume. Additionally, uncoated glass bubbles (Scotchlite™ K37) were added to the epoxy mixture at a level of 27% by volume. A cylinder of coated particle loaded epoxy composition was prepared by injecting the epoxy into a plastic tube having a length of about 72 mm and an inner diameter of about 16 mm, and then allowing the epoxy composition to cure. After the epoxy composition was cured, the plastic tube was removed. The hard epoxy polymer cylinder had a diameter of 15.9 mm and a length of 58 mm.

Figure 13:
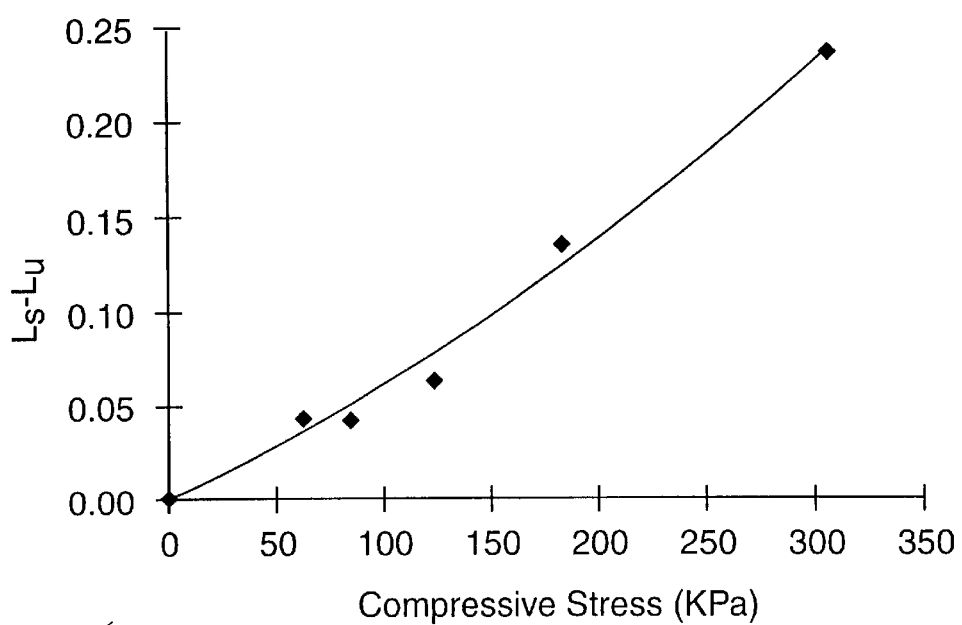
FIG. 13 is a plot of sample inductance (L stressed minus L unstressed) versus applied compressive stress.

The epoxy sample or cylinder was aligned vertically and supported by a plastic stand. The solenoid coil was placed over the epoxy sample such that the sample was contained within the coil. The initial inductance of the cylinder was measured and was 615.52 microHenry. Increasing amounts of force were applied to the sample cylinder to induce compressive stress. This was done as follows. Weights were added to a plastic platform that was attached to a wood rod. The distance between the metal weights and the top of the sample was 30 cm. The platform apparatus was slidably attached to a wall such that the platform with attached tube could move vertically with minimal friction. The wood rod was aligned with the vertical axis of the epoxy cylinder. The end of the rod contacted a glass sphere contained on a ceramic washer sitting on top of the sample cylinder. The applied weights were 1257, 2512, 3732, and 6145 g and the inductance ($L_s$ (stressed)) was measured at each applied weight. The initial inductance ($L_u$ (unstressed)) was subtracted from the inductance ($L_s$) reading at each applied weight and the applied weights were converted to compressive stress (static). FIG. 13 shows the resulting plot of the change in inductance of the sample due to the applied load versus the applied stress.

FIG. 13 shows that as compressive strength is increased, the inductance increases monotonically. This demonstrates that the method of the invention can be used to measure stress applied to a polymer or other material.

Example 17

The cylindrical epoxy test sample described in Example 16 was used in this test.

Figure 14:
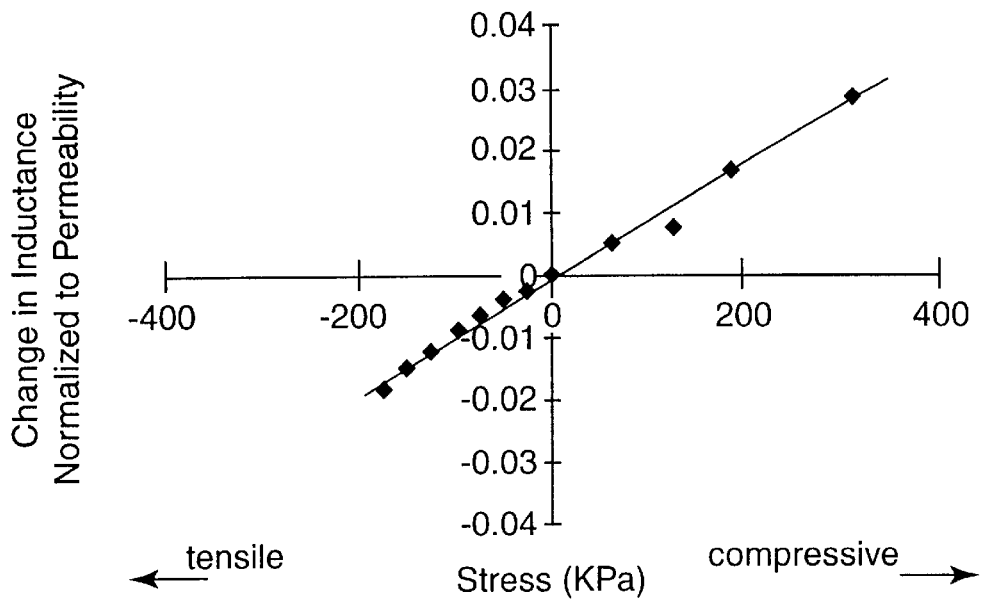
FIG. 14 is a plot of the change in inductance normalized to permeability versus applied stress (tensile and compressive).

The epoxy test cylinder was aligned vertically and affixed at the top end to a dielectric support using a fibrous tape. An attachment loop was fashioned from fibrous tape and the loop was attached to the bottom end of the epoxy cylinder. The solenoid coil of Example 16 was placed over the epoxy cylinder such that the cylinder was contained within the solenoid coil. A plastic bucket was then hooked onto the tape loop and water was added to provide the different test weights. The different test weights were 514, 1006, 1509, 1977, 2501, and 3511 grams. The weights were converted to an applied tensile stress (kPa). The empty coil inductance ($L_e$) was 606.74 microHenry and the unstressed inductance ($L_u$) of the epoxy cylinder was 615.05 microHenry. The change in inductance normalized to permeability was calculated using the following formula: $(L_s-L_u)/(L_u-L_e)$. The change in inductance normalized by permeability was plotted versus the applied stress. The results of the tensile test above and of Example 16 are shown in FIG. 14.

The data show that the inductance due to the inverse magnetostrictive effect of the sample changes linearly with externally applied tensile and compressive (static) stress.

Examples 18–23

The compressive stress test described in Example 16 was used to evaluate other magnetic particles, except that the applied weight was 3700 g. The epoxy cylinder samples of Examples 18–23 and comparative samples C1–C11 were prepared using methods similar to those described in Example 16. The coated particles of Examples 18–23 were made using methods similar to those described in Example 1.

Glossary for Table 1

SS/K37 is stainless steel coated glass Scotchlite™ K37 microbubbles. Examples 18 and 19 had an average stainless steel coating thickness of 23 nm. Example 20 had an average stainless steel coating thickness of 59 nm. Example 21 had an average stainless steel coating thickness of 86 nm.

Ni/C15 bubbles is nickel coated glass Scotchlite™ C15/250 glass microbubbles having a coating thickness of 10 nm. (Uncoated glass bubbles available from Minnesota Mining and Manufacturing Company, St. Paul, Minn.).

The glass fiber used in Example 23 and comparative examples C1, C2, and C3 is 731-ED 1/32 inch Milled Glass Fibers, commercially available from Owens Corning, Toledo, Ohio.

Ni/GF is nickel coated glass fiber having a coating thickness of 11 nm.

Co/GF is cobalt coated glass fiber described in Example 5.

Super invar/GF is super invar coated glass fibers having a coating thickness of 4 nm. The super invar composition is Fe(64)Ni(31)Co(5).

Permalloy™/GF is permalloy alloy coated glass fibers having a coating thickness of 10 nm. The permalloy composition is typically Ni(80)Fe(20).

Steward Ferrite is nickel zinc copper ferrite powder (product number 74002) and is commercially available from Steward Ferrites, Chattanooga, Tenn.

Iron Powder is FCC food grade reduced iron powder, available from J. T. Baker Chemical Co., Phillipsburg, N.J.

Nickel Powder is nickel powder (200 mesh) item number NX300, available from Matheson Coleman & Bell, Norwood, Ohio.

Magnetite is ferrosoferric oxide, black powder, item number CB387, available from Matheson Coleman & Bell, Norwood, Ohio.

410L is solid stainless steel particles, part number 11088, available from Alfa Aesar, Johnson Mathey, Ward Hill, Mass.

Ni:Fe 80:20 is nickel(80 wt %) iron (20 wt %) powder (100 mesh), item number 85501, available from Alfa Aesar, Johnson Mathey, Ward Hill, Mass.

Ni:Fe 50:50 is nickel(50 wt %) iron (50 wt %) powder, item number 88380, available from Alfa Aesar, Johnson Mathey, Ward Hill, Mass.

Lignosite FML is an aqueous dispersion of magnetite stabilized with lignosulfonate available from Georgia Pacific, Atlanta Ga. The water was removed by spray drying to form a solid powder.

| Ex. No. | Particle Type | Loading % v/v (wt %) | $L_u-L_e$ ($\mu H$) | $L_s-L_u$ ($\mu H$) | Change in Inductance Normalized to Loading | Change in Inductance Normalized to Permeability (ppt) |
|---|---|---|---|---|---|---|
| 18 | SS/K37 | 13 | 7.89 | .16 | 1.23 | 20 |
| 19 | SS/K37 | 40 | 23.93 | .35 | 0.88 | 15 |

-continued

| Ex. No. | Particle Type | Loading % v/v (wt %) | $L_u-L_e$ (μH) | $L_s-L_u$ (μH) | Change in Inductance Normalized to Loading | Change in Inductance Normalized to Permeability (ppt) |
|---|---|---|---|---|---|---|
| 20 | SS/K37 | 40 | 40.66 | .62 | 1.55 | 15 |
| 21 | SS/K37 | 40 | 51.07 | .79 | 1.98 | 15 |
| 22 | Ni/C15 | 50 (13) | 3.97 | −.16 | −0.32 | 40 |
| 23 | Ni/GF | 20 (35) | 10.52 | −.07 | −0.35 | 7 |
| C1 | Co/GF | 20 (36) | 6.46 | .00 | 0 | 0 |
| C2 | super invar/GF | 20 (35) | 7.03 | .01 | 0.05 | 1 |
| C3 | permalloy /GF | 20 (35) | 17.44 | −.01 | −0.05 | 1 |
| C4 | Lignosite FML | 5 (8) | 20.32 | .03 | 0.60 | 1 |
| C5 | Steward ferrite | 5 (19) | 60.29 | 0 | 0 | 0 |
| C6 | Nickel powder | 5 (28) | 64.47 | .04 | −0.80 | 1 |
| C7 | magnetite | 5 (7) | 37.7 | −.02 | −0.40 | 1 |
| C8 | 410L SS | 5 (25) | 86.66 | −.01 | 0.20 | 0 |
| C9 | Ni:Fe 50:50 | 5 (26) | 90.30 | .02 | 0.40 | 0 |
| C10 | Ni:Fe 80:20 | 5 (27) | 85.40 | .04 | 0.80 | 0 |
| C11 | Iron powder | 5 (25) | 84.64 | −.01 | 0.20 | 0 |

$L_u$=the inductance of the solenoid coil containing the sample containing the particular magnetic particles with no applied load.

$L_e$=the inductance of the solenoid coil containing no sample.

$L_s$=the inductance of the solenoid coil containing the sample containing the particular magnetic particles with an applied load of 3700 g.

$L_u-L_e$=a measure of the amount of inductance due the presence of the magnetic particles.

$L_s-L_u$=a measure of the change in inductance due to the applied load.

Change in Inductance Normalized to Loading is $(L_s-L_u)$/loading fraction and is a measure of the change in magnetic property normalized to the volume loading of the magnetic particles present.

Change in Inductance Normalized to Permeability is the ratio $(L_s-L_u)/(L_u-L_e)$, which normalizes the effect of the applied load to the signal due to the magnetic particles in the sample. This is expressed in parts-per-thousand (ppt).

The data in Table 1 show that coated particles can provide performance similar to that of solid particles even though the coated particles contain much less magnetic material. The samples containing cobalt and permalloy have the expected low magnetostrictive effect. For example, permalloy is designed to have a low magnetostrictive effect for use in electrical transformer cores to minimize noise. Cobalt is also known to have a low magnetostrictive response at low applied fields.

Examples 19–21 show that as the thickness of the metal coating increases, the change in inductance normalized to loading increases.

The data in Table 1 also demonstrate that both signs of inverse magnetostriction can be seen. The data also show that both spherical and acicular coated particles show the inverse magnetostriction effect. The data also demonstrate that the relative inverse magnetostrictive effect for coated particles, as measured by the change in inductance normalized to permeability, is larger than the effect for solid particles.

Examples 24–27

The epoxy cylinder samples of Examples 24–27 were prepared using Devcon™ 5-minute epoxy as described in Example 16. Examples 24–27 contained coated particles that were prepared as described in Example 1. The coated particles of Examples 24–27 had metal coating thicknesses of 23 and 10 nm, respectively. The volume loading of the coated particles in each sample is described in Table 2 below.

Examples 24–27 were subjected to a torsional stress. The resulting stress produced a change in inductance due to the inverse magnetostrictive effect.

The test apparatus was as follows. Test samples prepared as described in Examples 16 and 17 were oriented horizontally. On each end of each sample was bonded a wood square. The wood square at one end was inserted into a square hole in a fixed wooden block to prevent the cylinder from rotating. The wood square at the other end was inserted into a square hole in a wood level arm 30 cm in length, which was also oriented horizontally. Weight could be added to the end of the arm. The added weight exerts a torque on the cylinder, creating a torsional stress. Weights of 160 and 325 g were added, creating torques of approximately 0.47 and 0.96 N-m. The solenoid coil and RCL meter described in Example 16 were used.

| Ex. No. | Particle Type | Loading (% v/v) | Torque (N-m) | $L_u-L_e$ (μH) | $L_s-L_u$ (μH) | Change in Inductance Normalized to Loading | Change in Inductance Normalized to Permeability (ppt) |
|---|---|---|---|---|---|---|---|
| 24 | SS/K37 | 40 | 0.47 | 34.7 | −0.36 | −0.09 | −10 |
| 25 | SS/K37 | 40 | 0.96 | 34.7 | −1.49 | −3.7 | −43 |
| 26 | Ni/C15 | 50 | 0.47 | 5.61 | −0.66 | −1.3 | −118 |
| 27 | Ni/C15 | 50 | 0.96 | 5.61 | −1.49 | −1.9 | −266 |
| C12 | Ni Powder | 40 | 0.47 | 888.9 | 0.50 | 1.3 | 1 |
| C13 | Ni Powder | 40 | 0.96 | 888.9 | 0.80 | 1.6 | 1 |

The results are shown in Table 2 above. The measured values and the calculated values have the same definitions as described in Table 1 except that in Table 2, $L_s$=the inductance of the coil containing the sample at an applied load of 160 or 325 g. The data show that the coated particles provided a significant increase in the magnitude of the change in inductance normalized to permeability as torque was increased. In contrast, the solid nickel particles (C12 and C13) show a relatively insignificant change in inductance normalized to permeability.

Example 28

The degree of cure of a polymer was monitored using the measurement of inductance.

A cylinder of epoxy containing stainless steel microbubbles was prepared as described in Example 16 except that the sample was prepared in a glass tube (15.9 mm o.d., 13.6 mm i.d.) which fit inside the glass tube supporting the solenoid coil (0.6 millihenry). The stainless steel coated glass bubbles were prepared as described in Example 1 and they had a coating thickness of 23 nm. After mixing of the epoxy and the coated and uncoated glass bubbles, the epoxy composition was allowed to cool to room temperature and then the sample was placed into the solenoid coil. The inductance of the sample was monitored over a period of about 25 hours.

Figure 15:
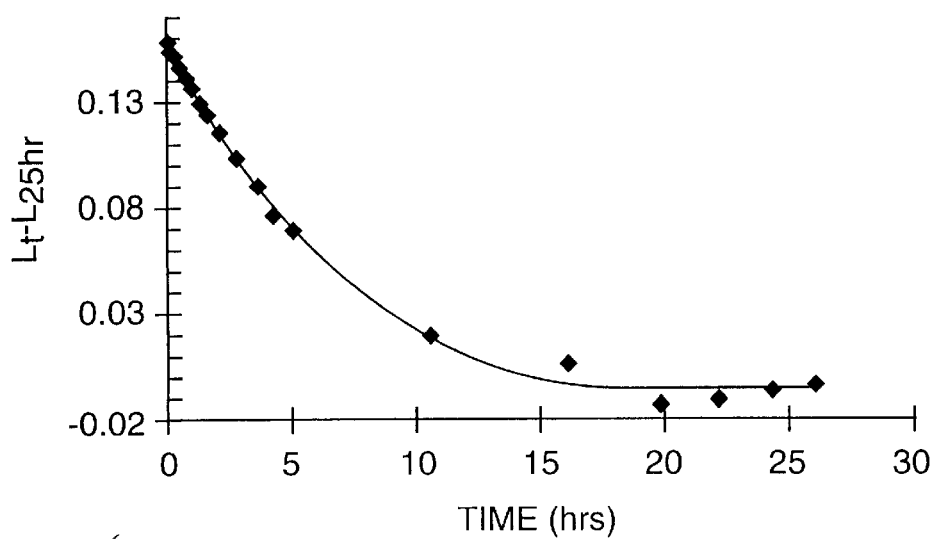
FIG. 15 is a plot of the sample inductance during cure minus the sample inductance after 25 hours of cure versus time of cure.

A plot of the difference between the sample inductance during cure ($L_t$) and the sample inductance after 25 hours ($L_{25hrs}$) versus time is shown in FIG. 15. This was calculated using the following expression: ($L_t$-$L_{25hrs}$). The data clearly show that the inductance decreases with time. As the epoxy adhesive cures, it progresses from being a liquid to a paste to a flexible solid to a hard solid. As the epoxy cures, it applies more stress to the magnetic coating on the bubbles, changing the magnetic permeability of the coating. The data demonstrate that a change in the internal stress level of the polymer can be detected or measured as the polymer becomes increasingly crosslinked or cured.

Example 29

In this example the dependence of inductance on temperature was measured.

Figure 16:
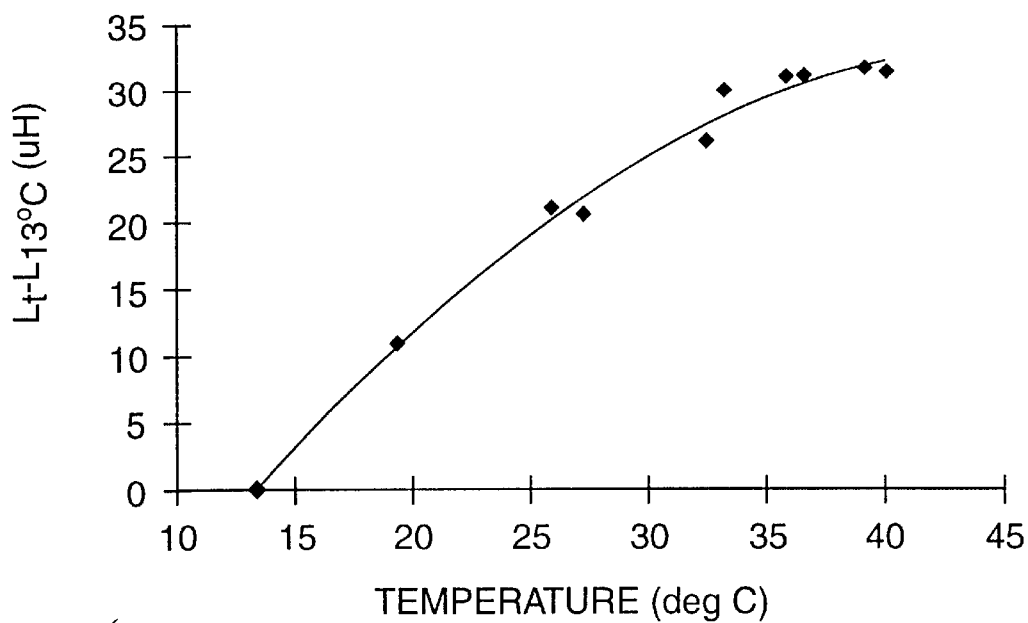
FIG. 16 is a plot of inductance of a sample minus the sample inductance at 13° C. versus temperature of the sample.
Figure 17:
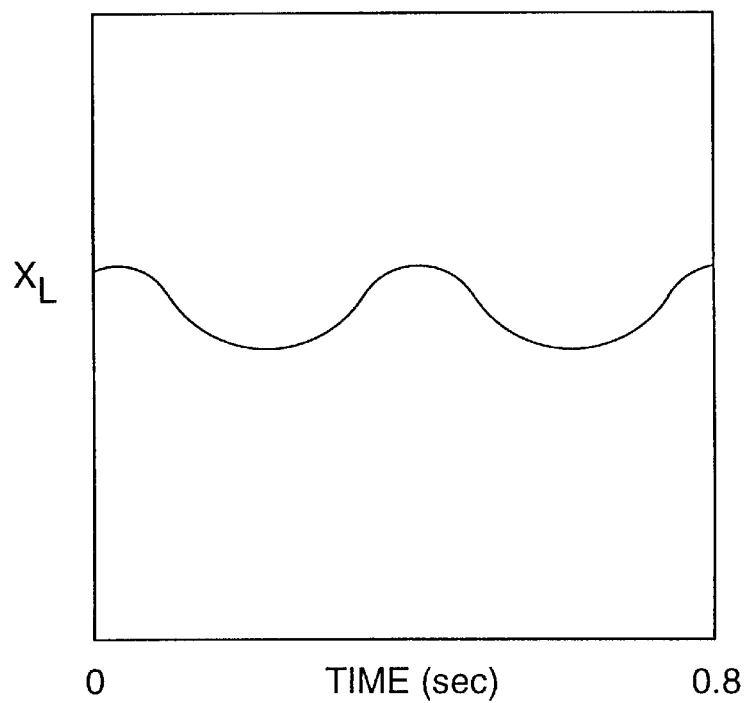
FIG. 17 is a plot of the Eddyscope™ response versus time for a sample subjected to an oscillating sinusoidal wave input at a frequency of 2 hertz.
Figure 18:
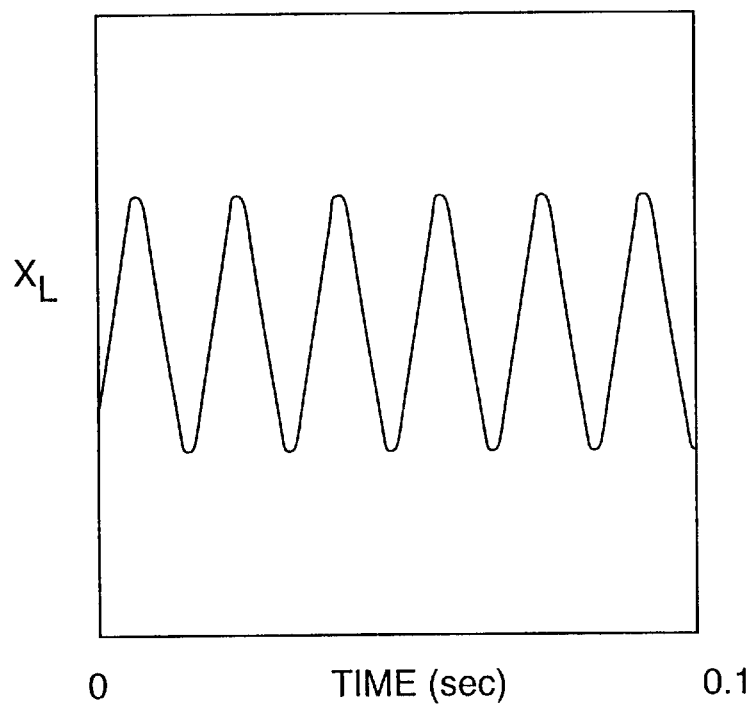
FIG. 18 is a plot of the Eddyscope™ response versus time for a sample subjected to an oscillating sinusoidal wave input at a frequency of 60 hertz.
Figure 19:
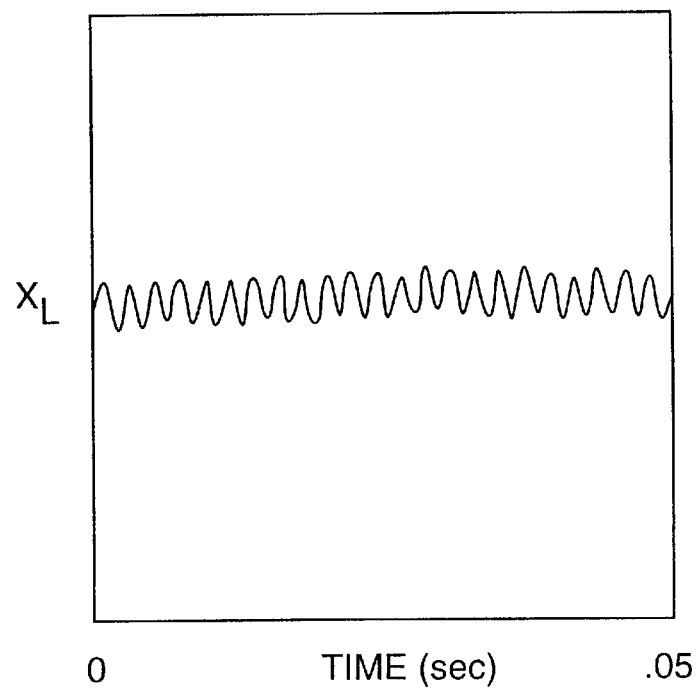
FIG. 19 is a plot of the Eddyscope™ response versus time for a sample subjected to an oscillating sinusoidal wave input at a frequency of 500 hertz.
Figure 20:
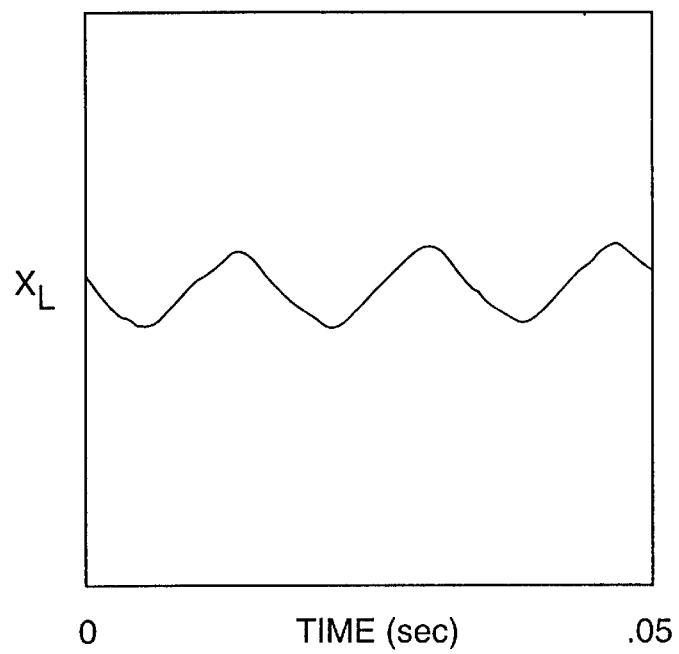
FIG. 20 is a plot of the Eddyscope™ response versus time of a sample subjected to an oscillating triangular wave input at a frequency of 60 hertz.

A cylindrical epoxy sample was prepared as described above in Example 16. Devcon™ 5 minute epoxy was used to make a sample having a 27 percent volume loading of Scotchlite™ K37 glass bubbles and 13 volume percent of the glass bubbles having a stainless steel coating 23 nm thick and prepared as described in Example 16. The solenoid coil used to measure inductance was similar to the solenoid coil described in Example 16 except that a total of 1060 turns (4 layers) were used over a length of 42 mm, giving an empty coil inductance ($L_e$) of about 9 milliHenry. The fully cured sample was heated in an oven at a known temperature, placed in an insulated cell fitted with a thermocouple so as to accurately determine the equilibrium temperature of the sample, then quickly inserted into the room temperature solenoid coil, where the inductance was recorded within a few seconds. The sample was then withdrawn from the solenoid coil and then heated to the next temperature. The inductance measurements were taken quickly so as to minimize the transfer of heat from the sample to the solenoid coil. The inductance measurement of the sample was repeated at each sample temperature. The solenoid coil measurements were not compensated for environmental temperature changes. The plot of the change in inductance versus sample temperature is shown in FIG. 16. The change in inductance was calculated using the following expression: $L_T$-$L_{13°\ C.}$.

The trend of the data for stainless steel coated glass bubbles shows that inductance increases with increasing sample temperature. The trend of the data appears to be related to inverse magnetostriction. The trend of the data is consistent with increasing relaxation of the epoxy matrix as temperature increases. The increase in temperature softens the polymer and relaxes the stress in the polymer system. The increased inductance associated with less stress in the sample (relaxation at higher temperature) is consistent with the results of Example 28. In Example 28, the inductance of the sample is also highest when the sample has the lowest level of stress (before the indicated full cure).

Comparison Example C13

The test above was repeated for a sample having a matrix of RTV 615 silicone rubber, available from General Electric Silicone, Waterford, N.Y. Stainless steel coated glass microbubbles as described above in Example 29 and present in the same amount by volume in Example 29 were used in the silicone rubber matrix. The silicone rubber matrix is softer and more rubbery after curing, when compared to the epoxy polymer used above.

The silicone rubber sample was expected to cure with much less stress, and so the temperature dependence of the inductance was expected to be much less that that of the epoxy sample above. In this Comparative Example, the observed temperature dependence of the inductance was only about 20% of that observed for the epoxy polymer measured above. Part of the observed dependence on temperature of the inductance for the silicone rubber sample may be due to heat transfer from the sample to the solenoid coil.

Example 30

An apparatus to apply an oscillating stress to a cylindrically shaped test sample was constructed. The apparatus consisted of a voice coil as a component in a subwoofer (12-inch dual voice coil subwoofer, cat. No. 40-1350A, from Radio Shack, Fort Worth, Tex.) with the magnet housing firmly attached to a massive cement building block. Portions of the subwoofer cone were removed with enough of the cone left to provide mechanical support for the mechanically floating voice coil. A wood rod was partially inserted into the bore of the voice coil and adhesively bonded thereto. The rod had a length of approximately 61 cm and a diameter of 1.6 cm. The rod was then adhesively bonded at the opposite end to one end of a test sample. The opposite end of the test sample was then adhesively bonded to a second massive cement building block. Both the test rod and the test sample were oriented horizontally and together formed a continuous rod, which was laterally constrained. The test sample was firmly affixed to the Eddyscope™ probe with an adhesive so as to prevent the influence of perpendicular forces on the Eddyscope™ output.

A metal spring having a known force constant was used to measure the amplitude of the applied oscillating stress. The spring was 6 cm in length and 1.9 cm in diameter with 9 turns and a force constant of 400 g/mm. The spring was inserted into a gap in the rod and mechanically affixed at both ends to the rod. The displacement of the spring was observed and recorded. This measurement was used to determine the maximum stress amplitude applied using Hooke's Law. The spring was removed from the apparatus and the rod was bonded directly to the sample when the oscillating triangular (non-sinusoidal) stress was directed to the voice coil. The removal of the spring was required so as to be able to fully resolve the triangular curve shape on the Eddyscope™.

The voice coil was driven by a stereo amplifier (Model STAV-3570, from Radio Shack). The input signal to the amplifier was provided by a signal generator (Wavetek Model 135 Lin/Log Sweep Generator, San Diego Calif.). A Nortec 19e$^{II}$ Eddyscope™ (Stavely Instruments, Kennewick, Wash.) with the model OD probe was used to measure the sample response. The Eddyscope™ settings were as follows: frequency=200 kHz; rotation=347°; probe drive=HI; vertical gain=90.0 dB. The time axis of the Eddyscope™ was expanded to include detection of time periods of about 0.001 seconds. This corresponds to frequencies up to 1000 Hz.

The test sample was an epoxy cylinder containing 40% v/v stainless steel coated Scotchlite™ K37 glass bubbles in epoxy polymer prepared as described in Example 16. The glass bubbles had an average coating thickness of 23 nm.

The epoxy sample was tested as follows. After the sample was secured in the apparatus as described above, a sine wave of known frequency was generated by the signal generator and input into the voice coil. The voice coil response was transmitted through the rod to the sample to produce an applied sinusoidally oscillating stress of known frequency on the sample. The maximum amplitude of the applied stress was 160 kPa and was determined by using the above described spring. The applied stress resulted in a sinusoidal response as measured with the Eddyscope™. Frequencies of from 1 to 1000 hertz were examined.

The Eddyscope™ outputs for several frequencies, 2, 60, 500, and 60 hertz, respectively, are shown in FIGS. 17–20.

The results show that the inverse magnetostrictive response of a polymer system containing magnetic particles can follow high frequency (acoustic) input accurately. The polymer system was shown to be effective as a transducer to convert the frequency of a mechanical signal to a magnetic signal having the same frequency.

Example 31

In this example, detection of the direction of stress in a polymer was demonstrated.

Stainless steel coated milled glass fibers (Fiberglas™ Milled Fibers 731ED 1/32 inch, Owens Corning, Toledo, Ohio) were dispersed at 20% v/v into Devcon™ 5 minute epoxy. The fibers were coated as described in Example 1 and had an average coating thickness of 22 nm. This mixture was injected into a plastic tube as described in Example 16. The plastic tube was then placed between two parallel barium ferrite ceramic bar magnets (parallel to the bars) and the epoxy was allowed to cure. After the epoxy had hardened, the plastic tube was removed, forming a cylindrically shaped epoxy sample. Since the magnetic field was perpendicular to the axis of the tube, the magnetic fibers were permanently aligned perpendicular to the axis of the sample. The fiber orientation was clearly visible under a low power microscope.

A second epoxy cylinder was prepared as described above, except that the magnets were placed further apart so that the plastic tube containing the sample composition was placed between and perpendicular to the magnetic bars. This sample orientation caused the magnetic fibers to align parallel to the axis of the sample during sample curing resulting in the magnetic fibers being permanently aligned parallel to the axis of the sample.

Both of the epoxy samples were subjected to the compressive test as described in Example 16. The applied mass was 4.2 kg. The empty test coil had an inductance of 901.57 microHenry and the initial inductance contribution of the sample containing fibers oriented parallel to the direction of applied stress was 33.38 microHenry. After the above stress was applied to the above sample, the change in inductance was +0.08 microHenry (a 0.24% increase). When subjected to the same applied stress, the change in inductance of the sample containing the perpendicular fibers was –0.03 microHenry (0.10% decrease). The initial inductance contribution of the sample containing the perpendicular fibers was 28.63 microHenry.

The primary direction of magnetization of the fibers was parallel to the fiber axis. When the stress was applied parallel to the parallel fibers, the inductance increased. When the stress was applied perpendicular to the fiber axis, the inductance decreased. The change in inductance indicated the direction of the particular applied stress relative to the fiber axis.

More generally, the above results demonstrate that the inductance change of magnetic coated fibers contained within a polymer that are inverse magnetostrictively active can be used to determine the direction of an applied or an internal stress.

Examples 32–33

This example demonstrated that adhesive bonding to the surface of a substrate influences the inductance of the adhesive via inverse magnetostriction.

The inside walls of three Pyrex™ glass tubes were treated with various organosilanes (available from OSi Specialties, Inc., Danbury Conn.). Organosilanes are composed of a silane end and an organic end. The silane end will bond to glass. In Example 32, the organic moiety of the organosilane is an octyl group which is not expected to covalently bond to the epoxy. In Example 33, the organic moiety of the organosilane is an glycidoxy propyl group which is chemically similar to the epoxy component of the adhesive, and so is expected to covalently bond to the epoxy adhesive through reaction with the curing agent.

The above glass tubes were treated with organosilane as follows. An octyl-silane solution was prepared by adding 3.96 grams of octyltrimethoxysilane and 0.99 grams of n-propylamine to 396 grams of acetone. An epoxy silane solution was prepared in the same manner except that 2.78 grams of gamma-glycidoxypropyltrimethoxysilane was used in place of the octyltrimethoxysilane. Each glass tube to be treated was added to the solution contained in a beaker and allowed to stand for 30–40 hours. Each tube was removed and then stored in a vacuum for at least 10 hours.

Inverse magnetostrictive stainless steel coated Scotchlite™ K37 glass bubbles were prepared as described in Example 1 and were mixed at a volume loading of 40% into an epoxy formulation prepared at a weight ratio of 10.0 g of Epon™ 828 and 5.66 g of a commercially available curing agent (Ancamine™ AD, from Air Products and Chemicals, Inc., Allentown, Pa.). The resulting mixture was injected into the surface treated glass tubes described above. The cure of each epoxy adhesive was followed with a solenoid coil as in Example 28 above.

A comparison of the bonded vs. non-bonded cure was made. Bonding to the glass substrate can induce stresses in the epoxy which can be detected by the inverse magnetostriction effect. For the glass tube treated with octyl-terminated silane (Example 32), the epoxy cylinder detached from the tube during cure (after 75 minutes). This coincided with an abrupt drop in the inductance of 3.81 microHenry, a change in the inductance due to the sample of 14%. After the detachment of the epoxy cylinder, the inductance began to slowly rise.

Figure 21:
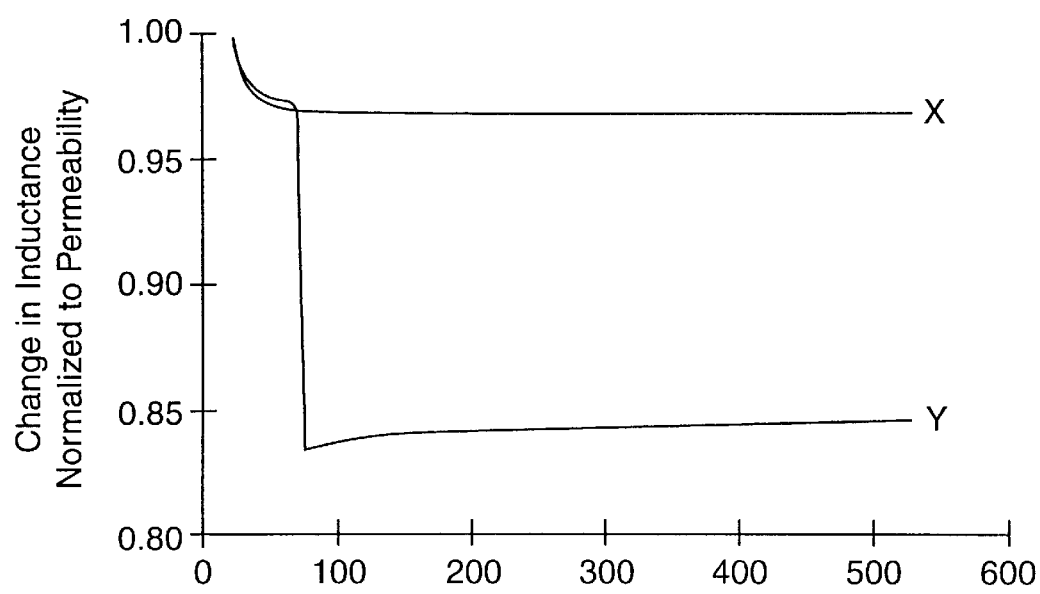
FIG. 21 is a plot of the change in inductance normalized to sample permeability versus time for two epoxy adhesive samples during curing.

For the sample treated with epoxy-terminated silane (Example 33), the epoxy cylinder remained attached and the inductance gradually dropped analogously to the inductance in Example 28. For each sample, the change in inductance normalized to permeability was determined. This was done using the following expression: $(L_t-L_e)/(L_{21\ min}-L_e)$. This was plotted versus time. The samples were mixed at t=0, allowed to cool to the point they would not heat the coil, inserted into the coil, then inductance measurement was started. These data are shown in FIG. 21 as curve "X" for Example 33 and curve "Y" for Example 32.

The results indicate that such inverse magnetostrictive systems can be used to detect adhesion failure. The relief of stress at the epoxy-glass interface bond was accompanied by a change in stress in the bulk epoxy sample. This was seen in the inductance of the solenoid coil containing the inversely magnetostrictive epoxy sample. The detachment of the epoxy sample from the glass may have led to a decrease in the volume of the sample, but this effect was determined to be minor.

This example demonstrates that the degree of adhesion to a surface can be determined using inverse magnetostrictive tags.

Example 34

This example demonstrates detection of stress in a thermoplastic polymer.

Stainless steel coated glass microbubbles prepared as described in Example 1 and having a coating thickness of 23 nm were mixed with polystyrene resin pellets (Styron™ XL-8028, from The Dow Chemical Company, Midland, Mich.), at a volume loading of 20%. The mixture was heated to approximately 260 degrees centigrade and the bubbles were blended into the polystyrene resin. The hot liquid mixture was then pressed into a heated metal tube lined with a paper release liner. Upon cooling, the polystyrene cylinder sample was removed from the metal tube.

The polystyrene sample was tested as described in Example 16. An applied compressive load of 4.2 kg resulted in a change in inductance normalized to permeability of +17 ppt.

Equivalents

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method for determining the level of stress in a polymeric or pre-polymeric composition within a given volume comprising the steps of:
   (a) providing a polymeric or pre-polymeric composition containing a plurality of microparticles comprising a non-ferromagnetic or non-ferrimagnetic core provided with a coating that is ferromagnetic or ferrimagnetic, or a combination thereof wherein said microparticles are substantially uniformly dispersed throughout said composition,
      said microparticles having a detectable magnetic characteristic which correlates with the level of stress in the composition within a given volume; and
   (b) measuring said magnetic characteristic of said microparticles to determine said level of stress in said composition within a given volume.

2. The method of claim 1, wherein said core of said microparticles is selected from the group consisting of glass bubbles, glass beads, glass fibers, fumed silica particles, fused silica particles, mica flakes, polymeric particles, and combinations thereof.

3. The method of claim 1 wherein said core of microparticles comprises a glass bubble.

4. The method of claim 1 wherein said magnetic characteristic is magnetic permeability.

5. The method of claim 1 wherein said coating comprises stainless steel.

6. The method of claim 1 wherein said microparticles comprise metal-coated glass bubbles wherein said metal coating is ferrimagnetic or ferromagnetic.

7. The method of claim 1 wherein said coating comprises a ferromagnetic or ferrimagnetic composition selected from the group consisting of nickel, iron, alloys thereof and oxides thereof.

8. The method of claim 1 wherein said microparticles have an average major dimension between about 10 micrometers to about 1 millimeter.

9. The method of claim 1 wherein said coating has an average thickness ranging from about 0.1 nanometers to about 5 micrometers.

10. The method of claim 1 wherein said coating has an average thickness ranging from about 1 nanometer to about 200 nanometers.

11. The method of claim 1 wherein said coating is in the form of a substantially continuous coating on said core.

12. The method of claim 1 wherein said composition contains between about 0.01% and about 80% by volume of said microparticles.

13. The method of claim 1 wherein the stress level in the composition containing said microparticles is used to determine the degree of cure of said composition.

14. The method of claim 1 wherein the stress level in the composition containing said microparticles is used to determine the level of external forces applied to said composition.

15. The method of claim 1 wherein said polymeric or pre-polymeric composition is an adhesive.

16. The method of claim 1 wherein said polymeric or pre-polymeric composition is a thermosetting or a thermoplastic material.

17. The method of claim 16 wherein the level of stress in the composition containing said microparticles is used to determine the thermal history of said composition.

18. The method of claim 15 wherein the stress level in the adhesive containing said microparticles is used to determine the amount of adhesion of the adhesive to a substrate.

19. The method of claim 1 wherein the stress level in the composition containing said microparticles is used to determine the direction of the stress in the composition.

20. The method of claim 1 wherein said measured magnetic characteristic is inductance.

21. The method of claim 1 wherein said measured magnetic characteristic is inductive reactance.

22. The method of claim 1 further comprising the step of correcting the measurement of said magnetic characteristic for temperature.

23. The method of claim 1 wherein said polymeric composition is selected from the group consisting of epoxy resins, polyurethanes, and acrylates.

24. The method of claim 23 comprising depositing said composition containing said microparticles on a substrate and measuring the magnetic characteristic of said microparticles to determine the level of stress in said composition.

25. The method of claim 1 wherein said polymeric or pre-polymeric composition containing said microparticles is an adhesive and wherein said level of stress is used to determine the amount of adhesion of said adhesive to a substrate.

26. The method of claim 1 wherein said polymeric or pre-polymeric composition containing said microparticles is an adhesive and wherein said level of stress is used to determine the quality of adhesion of said adhesive to a substrate.

27. The method of claim 1 wherein said polymeric or pre-polymeric composition containing said microparticles is an adhesive and wherein said level of stress is used to determine the amount of and quality of adhesion of said adhesive to a substrate.

28. A method for measuring the level of stress in a polymeric or a pre-polymeric composition within a given volume comprising the steps of:

(a) combining said polymeric or pre-polymeric composition with a plurality of microparticles comprising a non-fertomagnetic or non-ferrimagnetic core provided with a coating that is ferromagnetic or ferrimagnetic, or a combination thereof to form an admixture in which said microparticles are substantially uniformly dispersed throughout said composition, said microparticles having a detectable magnetic characteristic which correlates with the level of stress in the composition within a given volume, said magnetic characteristic selected from the group consisting of magnetic permeability, inductance, and inductive reactance; and (b) measuring said magnetic characteristic of said microparticles to determine said level of stress in said composition within a given volume.

29. The method of claim 28 comprising dispensing said admixture while measuring the magnetic characteristic of said microparticles to determine the stress level of said polymeric or pre-polymeric composition in said admixture being dispensed.

30. The method of claim 28 comprising combining a first polymeric or pre-polymeric composition with a second polymeric or pre-polymeric composition to form a reaction mixture, said method comprising combining at least one of said polymeric or pre-polymeric compositions with said microparticles prior to combining said first and second polymeric or pre-polymeric compositions together.

31. The method of claim 30 comprising measuring said magnetic characteristic of said microparticles in said reaction mixture.

32. The method of claim 30 comprising combining both of said polymeric or pre-polymeric compositions with said microparticles.

33. The method of claim 30 wherein said microparticles in said first polymeric or pre-polymeric compositions are different from said microparticles in said second polymeric or pre-polymeric composition.

34. A method for measuring the level of stress in a polymeric or pre-polymeric composition within a given volume comprising the steps of:

(a) combining said polymeric or pre-polymeric composition with a plurality of coated glass bubble microparticles, where said coating is ferromagnetic or ferrimagnetic to form an admixture in which said microparticles are substantially uniformly dispersed throughout said composition, said microparticles having a detectable magnetic characteristic which correlates with the level of stress in said composition within a given volume; and (b) measuring said magnetic characteristic of said microparticles to determine said stress level of said composition within a given volume.

* * * * *